(12) United States Patent
Lau et al.

(10) Patent No.: US 9,012,398 B2
(45) Date of Patent: Apr. 21, 2015

(54) ACYLATED EXENDIN-4 COMPOUNDS

(75) Inventors: Jesper Lau, Farum (DK); Thomas K. Hansen, Herlev (DK); Leif Christensen, Roskilde (DK); Kjeld Madsen, Vaerlose (DK); Lauge Schaeffer, Lyngby (DK); Jane Spetzler, Broenshoej (DK)

(73) Assignee: Novo Nordisk A/S, Bagsvaerd (DK)

( * ) Notice: Subject to any disclaimer, the term of this patent is extended or adjusted under 35 U.S.C. 154(b) by 162 days.

(21) Appl. No.: 13/461,155

(22) Filed: May 1, 2012

(65) Prior Publication Data

US 2012/0283170 A1 Nov. 8, 2012

Related U.S. Application Data

(63) Continuation of application No. 12/438,280, filed as application No. PCT/EP2007/058789 on Aug. 24, 2007, now abandoned.

(60) Provisional application No. 60/840,808, filed on Aug. 29, 2006.

(30) Foreign Application Priority Data

Aug. 25, 2006 (EP) .................................. 06119570

(51) Int. Cl.
| | |
|---|---|
| *A61K 38/26* | (2006.01) |
| *C07K 14/605* | (2006.01) |
| *C07K 14/575* | (2006.01) |
| *A61K 47/48* | (2006.01) |
| *A61K 38/00* | (2006.01) |

(52) U.S. Cl.
CPC ............ *C07K 14/57563* (2013.01); *A61K 38/26* (2013.01); *A61K 47/48061* (2013.01); *C07K 14/605* (2013.01); *A61K 47/48046* (2013.01); *A61K 47/48038* (2013.01); *A61K 47/48215* (2013.01); *A61K 38/00* (2013.01)

(58) Field of Classification Search
None
See application file for complete search history.

(56) References Cited

U.S. PATENT DOCUMENTS

| | | |
|---|---|---|
| 6,451,974 B1 | 9/2002 | Hansen |
| 2001/0047084 A1 | 11/2001 | Knudsen et al. |
| 2002/0137666 A1 | 9/2002 | Beeley et al. |
| 2004/0203033 A1 | 10/2004 | Briggs et al. |
| 2006/0171920 A1 | 8/2006 | Shechter et al. |
| 2010/0009904 A1 | 1/2010 | Lv et al. |
| 2010/0029554 A1* | 2/2010 | Ghosh et al. .................... 514/12 |

FOREIGN PATENT DOCUMENTS

| | | |
|---|---|---|
| WO | 03/103572 | 12/2003 |
| WO | 2004/050115 A2 | 6/2004 |
| WO | 2004/056317 A2 | 7/2004 |
| WO | 2005/019261 A1 | 3/2005 |
| WO | 2005/027978 | 3/2005 |
| WO | 2005/046716 | 5/2005 |
| WO | 2005/058958 A2 | 6/2005 |
| WO | 2006/005667 A2 | 1/2006 |
| WO | 2006/037811 A2 | 4/2006 |
| WO | 2006/051103 | 5/2006 |
| WO | 2006074600 A1 | 7/2006 |

OTHER PUBLICATIONS

Holz, G. et al., Glucagon-Like Peptide-1 Synthetic Analogs: New Therapeutic Agents for use in the Treatment of Diabetes Mellitus, Current Medicinal Chemistry, vol. 10(22), pp. 2471-2483 (2003).
Tam, J. et al., Dual-Action Peptides: A New Strategy in the Treatment of Diabetes-Associated Neuropathy, Drug Discovery Today, vol. 11(5/6), pp. 254-260 (2006).

* cited by examiner

*Primary Examiner* — Jeffrey E Russel
(74) *Attorney, Agent, or Firm* — Richard W. Bork

(57) ABSTRACT

This invention provides Exendin-4 compounds derivatized at a lysine 14 residue to give an acylated lysine, pharmaceutical compositions comprising such compounds, and the use of such compositions for treating diabetes.

18 Claims, No Drawings

ACYLATED EXENDIN-4 COMPOUNDS

CROSS REFERENCE TO RELATED APPLICATIONS

This application is a continuation of U.S. application Ser. No. 12/438,280, filed Jun. 9, 2009, now abandoned, which is a U.S.C. §371 National Stage application of International Application PCT/EP2007/058789, filed Aug. 24, 2007 (published as WO2008/023050), which claimed priority of European Patent Application 06119570.7, filed on Aug. 25, 2006; and of U.S. Provisional Application 60/840,808, filed Aug. 29, 2006; the contents of which are fully incorporated herein by reference.

INCORPORATION-BY-REFERENCE OF THE SEQUENCE LISTING

In accordance with 37 C.F.R. §1.52(e)(5), Applicants enclose herewith the Sequence Listing for the above-captioned application entitled "SEQUENCE LISTING", created on Oct. 27, 2014. The Sequence Listing is made up of 14 kilobytes, and the information contained in the attached "SEQUENCE LISTING" is identical to the information in the specification as originally filed. No new matter is added.

FIELD OF THE INVENTION

This invention relates to the field of therapeutic peptides, i.e. to new protracted Exendin-4 compounds.

BACKGROUND OF THE INVENTION

In the last decade a number of peptides have been isolated from the venom of the Gila monster lizards (*Heloderma suspectum* and *Heloderma horridum*). Exendin-4 is a 39 amino acid residue peptide isolated from the venom of *Heloderma suspectum*, and this peptide shares 52% homology with GLP-1(7-37) in the overlapping region. Exendin-4 is a potent GLP-1 receptor agonist which has been shown to stimulate insulin release and ensuing lowering of the blood glucose level when injected into dogs. The group of exendin-4(1-39), certain fragments thereof, analogues thereof and derivatives thereof, are potent insulinotropic agents.

Many diabetes patients particularly in the type 2 diabetes segment are subject to so-called "needle-phobia", i.e. a substantial fear of injecting themselves. In the type 2 diabetes segment most patients are treated with oral hypoglycaemic agents, and since GLP-1 compounds and exendin-4 compounds are expected to be the first injectable product these patients will be administered, the fear of injections may become a serious obstacle for the widespread use of the clinically very promising compounds. Thus, there is a need to develop new compounds which can be administered less than once daily, e.g. once every second or third day preferably once weekly, while retaining an acceptable clinical profile. Optionally via pulmonal or nasal administration.

Exendin-4 is chemically labile due to Met14 oxidation and Asn28Gly29 deamidation. One object of the present invention is to provide a chemically stable derivative of exendins and analogues thereof. One object of the invention is to provide a long acting ie. having an administration regimen as described above—derivative of exendin or analogues thereof.

SUMMARY OF THE INVENTION

The invention provides a compound comprising the amino acid sequence of the formula (I):

(SEQ ID No: 1)
Xaa₁-Xaa₂-Glu-Gly-Thr-Xaa₆-Thr-Ser-Asp-Leu-Ser-Xaa₁₂-Gln-Xaa₁₄-Glu-Xaa₁₆-Xaa₁₇-Ala-Val-Xaa₂₀-Xaa₂₁-Phe-Ile-Xaa₂₄-Trp-Leu-Xaa₂₇-Xaa₂₈-Xaa₂₉-Gly-Pro-Xaa₃₂-Ser-Xaa₃₄-Ala-Pro-Pro-Pro-Xaa₃₉.
Formula (I)

wherein
Xaa₁ is L-histidine, imidazoylpropionyl, D-histidine, desamino-histidine, 2-amino-histidinehomohistidine, Nᵅ-acetyl-histidine, α-methyl-histidine, 3-pyridylalanine, 2-pyridylalanine or 4-pyridylalanine,
Xaa₂ is Ala, Gly or Aib;
Xaa₆ is Phe or α-methyl-Phe;
Xaa₁₂ is Lys, Arg or Gln;
Xaa₁₄ is Leu, Lys, Met, Ile or Nle;
Xaa₁₆ is Gly, Glu or Aib;
Xaa₁₇ is Gln or Glu;
Xaa₂₀ is Lys, Glu or Arg;
Xaa₂₁ is Glu or Leu;
Xaa₂₄ is Ala, Glu or Arg;
Xaa₂₇ is Val, Lys, Gln or Arg;
Xaa₂₈ is Lys, Leu, Glu, Asn, Gln or Arg;
Xaa₂₉ is Gly, Ala or Aib;
Xaa₃₂ is Ser or Lys;
Xaa₃₄ is Gly or Lys;
Xaa₃₉ is Ser or O-Benzyl-Ser
the C-terminal may optionally be derivatized as an amide; and wherein one lysine selected from Lys12, Lys14, Lys20, Lys27, Lys28, Lys32 or Lys 34 in formula I is derivatized with A-(B)ᵣ—(C)ₛ— to give an acylated Lys residue, wherein C, which is independently selected s times, where s is 0, 1, 2, 3 or 4, is represented by:

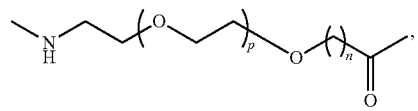

wherein p is 1, 2, 3, 4, 5, 6, 7, 8, 9, 10, 11, 12, 13, 14, 15, 16, 17, 18, 19, 20, 21, 22, or 23 and n is 1, 2, 3 or 4;
and wherein B is a group selected r times, where r is 0, 1, 2 or 3, from the group consisting of:

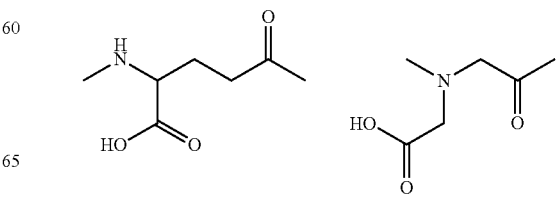

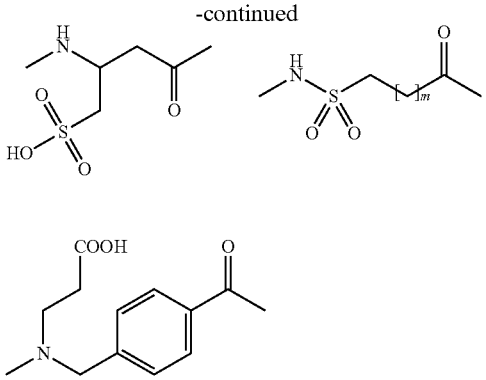

and
wherein A is a group selected from:

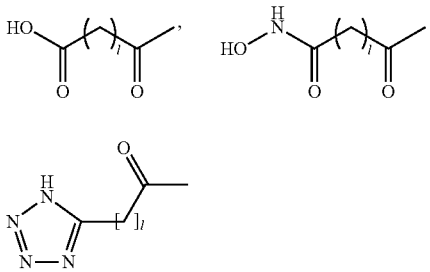

or CH3(CH$_2$)$_l$—C(=O)—.
where l is 12, 13, 14, 15, 16, 17, 18, 19 or 20
with the provisory that at least two amino acids selected from Xaa$_1$, Xaa$_2$, Xaa$_6$, Xaa$_{12}$, Xaa$_{15}$, Xaa$_{16}$, Xaa$_{17}$, Xaa$_{20}$, Xaa$_{21}$, Xaa$_{24}$, Xaa$_{27}$Xaa$_{28}$, Xaa$_{29}$, Xaa$_{32}$, Xaa$_{34}$ and Xaa$_{39}$
are different from the corresponding amino acid in exendin-4, The invention also provides a pharmaceutical composition comprising a compound according to any of the embodiments in the present invention, and a pharmaceutically acceptable excipient.

The invention also provides the use of a compound according to any one of the embodiments of the present invention for the preparation of a medicament.

The invention also provides the use of a compound according to any one of the embodiments of the invention for the preparation of a medicament for the treatment or prevention of hyperglycemia, type 2 diabetes, impaired glucose tolerance, type 1 diabetes, obesity, hypertension, syndrome X, dyslipidemia, cognitive disorders, atheroschlerosis, myocardial infarction, coronary heart disease and other cardiovascular disorders, CNS disorders such as Alzheimer's, stroke, inflammatory bowel syndrome, dyspepsia and gastric ulcers.

DESCRIPTION OF THE INVENTION

The invention provides a compound comprising the amino acid sequence of the formula (I):

wherein
Xaa$_1$ is L-histidine, imidazoylpropionyl, D-histidine, desamino-histidine, 2-amino-histidinehomohistidine, N$^\alpha$-acetyl-histidine, α-methyl-histidine, 3-pyridylalanine, 2-pyridylalanine or 4-pyridylalanine;
Xaa$_2$ is Ala, Gly or Aib;
Xaa$_6$ is Phe or α-methyl-Phe;
Xaa$_{12}$ is Lys, Arg or Gln;
Xaa$_{14}$ is Leu, Lys, Met, Ile or Nle;
Xaa$_{16}$ is Gly, Glu or Aib;
Xaa$_{17}$ is Gln or Glu;
Xaa$_{20}$ is Lys, Glu or Arg;
Xaa$_{21}$ is Glu or Leu;
Xaa$_{24}$ is Ala, Glu or Arg;
Xaa$_{27}$ is Val, Lys, Gln or Arg;
Xaa$_{28}$ is Lys, Leu, Glu, Asn, Gln or Arg;
Xaa$_{29}$ is Gly, Ala or Aib;
Xaa$_{32}$ is Ser or Lys;
Xaa$_{34}$ is Gly or Lys;
Xaa$_{39}$ is Ser or O-Benzyl-Ser
the C-terminal may optionally be derivatized as an amide;
and wherein one lysine selected from Lys12, Lys14, Lys20, Lys27, Lys28, Lys32 or Lys 34 in formula I is derivatized with A-(B)$_r$—(C)$_s$— to give an acylated Lys residue,
wherein C, which is independently selected s times, where s is 0, 1, 2, 3 or 4, is represented by:

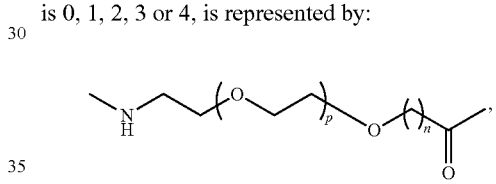

wherein p is 1, 2, 3, 4, 5, 6, 7, 8, 9, 10, 11, 12, 13, 14, 15, 16, 17, 18, 19, 20, 21, 22, or 23 and n is 1, 2, 3 or 4;
and wherein B is a group selected r times, where r is 0, 1, 2 or 3, from the group consisting of:

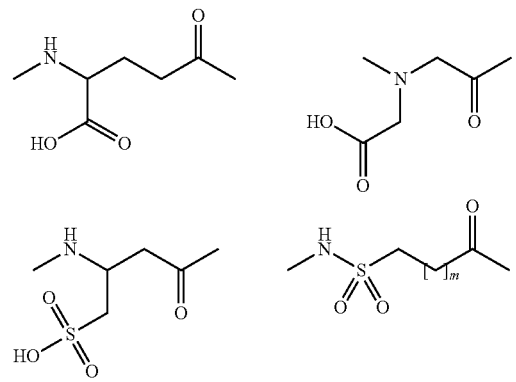

(SEQ ID No: 1)
Xaa$_1$-Xaa$_2$-Glu-Gly-Thr-Xaa$_6$-Thr-Ser-Asp-Leu-Ser-Xaa$_{12}$-Gln-Xaa$_{14}$-Glu-Xaa$_{16}$-Xaa$_{17}$-Ala-
Val-Xaa$_{20}$-Xaa$_{21}$-Phe-Ile-Xaa$_{24}$-Trp-Leu-Xaa$_{27}$-Xaa$_{28}$-Xaa$_{29}$-Gly-Pro-Xaa$_{32}$-Ser-Xaa$_{34}$-Ala-Pro-
Pro-Pro-Xaa$_{39}$.
Formula (I)

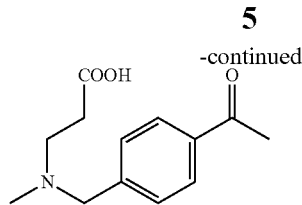

and
wherein A is a group selected from:

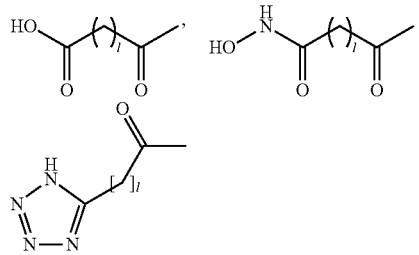

or CH3(CH$_2$)$_l$—C(=O)—.
where l is 12, 13, 14, 15, 16, 17, 18, 19 or 20
with the provisory that at least two amino acids selected from Xaa$_1$, Xaa$_2$, Xaa$_6$, Xaa$_{12}$, Xaa$_{15}$, Xaa$_{16}$, Xaa$_{17}$, Xaa$_{20}$, Xaa$_{21}$, Xaa$_{24}$, Xaa$_{27}$Xaa$_{28}$, Xaa$_{29}$, Xaa$_{32}$, Xaa$_{34}$ and Xaa$_{39}$ are different from the corresponding amino acid in exendin-4.

An embodiment of the invention provides a compound according formula (I) as disclosed above wherein
Xaa$_1$ is L-histidine, imidazoylpropionyl or des-amino Histidine;
Xaa$_2$ is Gly or Aib,
Xaa$_6$ is Phe or α-methyl-Phe;
Xaa$_{12}$ is Lys, Arg or Gln;
Xaa$_{14}$ is Leu, Lys or Met;
Xaa$_{16}$ is Glu;
Xaa$_{17}$ is Glu;
Xaa$_{20}$ is Lys;
Xaa$_{21}$ is Leu;
Xaa$_{24}$ is Glu;
Xaa$_{27}$ is Val, Lys, Gln or Arg;
Xaa$_{28}$ is Lys, Leu, Glu, Asn, Gln or Arg;
Xaa$_{29}$ is Gly or, Ala;
Xaa$_{32}$ is Ser or Lys;
Xaa$_{34}$ is Gly or Lys;
Xaa$_{39}$ is Ser or O-Benzyl-Ser
the C-terminal may optionally be derivatized as an amide;
and wherein one lysine selected from Lys12, Lys14, Lys20, Lys27, Lys28, Lys32 or Lys 34 in formula I is derivatized with A-(B)$_r$—(C)$_s$— to give an acylated Lys residue,
wherein C, which is independently selected s times, where s is 0, 1, 2, 3 or 4, is represented by:

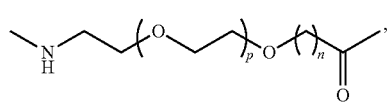

wherein p is 1, 2, 3, 4, 5, 6, 7, 8, 9, 10, 11, 12, 13, 14, 15, 16, 17, 18, 19, 20, 21, 22, or 23
and n is 1, 2 or 3;
and wherein B is a group selected r times, where r is 0, 1, 2 or 3, from the group consisting of:

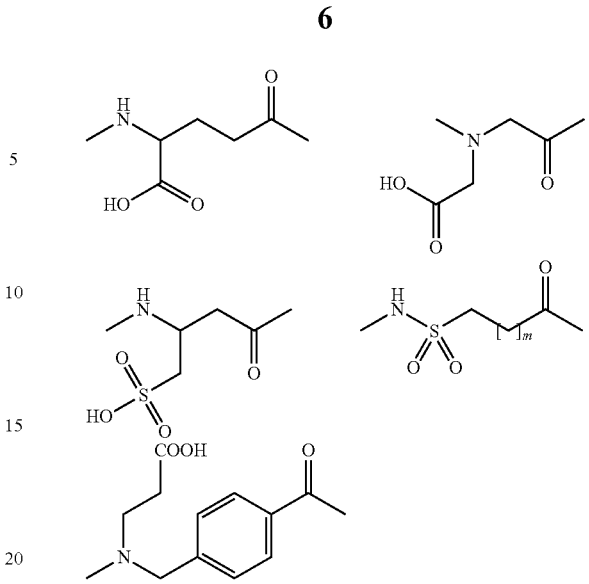

and
wherein A is a group selected from

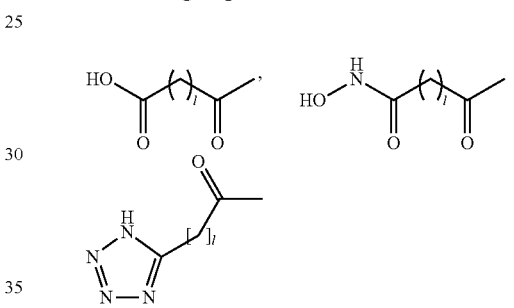

or CH3(CH$_2$)$_l$—C(=O)—.
where l is 12, 13, 14, 15, 16, 17, 18, 19 or 20

An embodiment of the invention provides a compound according to any of the above embodiments wherein Xaa$_{12}$ is Arg;

An embodiment of the invention provides a compound according to any of the embodiments above wherein Xaa$_{14}$ is Leu or Lys;

An embodiment of the invention provides a compound according to any of the embodiments above wherein Xaa$_{14}$ is Leu;

An embodiment of the invention provides a compound according to any of the embodiments above wherein Xaa$_{14}$ is Lys and wherein said Lys14 is derivatized with A-(B)$_r$—(C)$_s$— to give an acylated Lys residue;

An embodiment of the invention provides a compound according to any of the above embodiments wherein Xaa$_{20}$ is Lys;

An embodiment of the invention provides a compound according to any of the above embodiments wherein Xaa$_{28}$ is Gln, Leu, Arg, or Lys;

An embodiment of the invention provides a compound according to any of the above embodiments wherein Xaa$_{28}$ is Lys and wherein said Lys28 is derivatized with A-(B)$_r$—(C)$_s$— to give an acylated Lys residue;

An embodiment of the invention provides a compound according to any of the above embodiments wherein Xaa$_{28}$ is Gln;

An embodiment of the invention provides a compound according to any of the above embodiments wherein Xaa$_{29}$ is Ala;

An embodiment of the invention provides a compound according to any of the above embodiments wherein $Xaa_{14}$ is Leu or Lys and $Xaa_{28}$ is Lys, Leu, Gln or Arg An embodiment of the invention provides a compound according to any of the above embodiments wherein $Xaa_{14}$ is Leu or Lys and $Xaa_{29}$ is Ala or Aib;

An embodiment of the invention provides a compound according to any of the above embodiments wherein $Xaa_{14}$ is Leu or Lys and $Xaa_{29}$ is Ala;

An embodiment of the invention provides a compound according to any of the above embodiments wherein r is 1;

An embodiment of the invention provides a compound according to any of the above embodiments wherein s is 2, An embodiment of the invention provides a compound according to any of the above embodiments wherein p is 1.

An embodiment of the invention provides a compound according to any of the above embodiments wherein B is

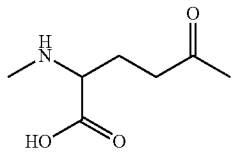

An embodiment of the invention provides a compound according to any of the above embodiments wherein A is or

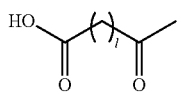

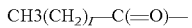

$CH3(CH_2)_l$—$C(=O)$—

An embodiment of the invention provides a compound according to any of the above embodiments wherein I is 13, 14, 15, 16, 17 or 18;

An embodiment of the invention provides the use of a compound according to any one of the above embodiments for the preparation of a medicament.

An embodiment of the invention provides the use of a compound according to any one of the above embodiments for the preparation of a medicament for the treatment or prevention of hyperglycemia, type 2 diabetes, impaired glucose tolerance, type 1 diabetes, obesity, hypertension, syndrome X, dyslipidemia, cognitive disorders, atheroschlerosis, myocardial infarction, coronary heart disease and other cardiovascular disorders, CNS disorders such as Alzheimer's, stroke, inflammatory bowel syndrome, dyspepsia and gastric ulcers.

An embodiment of the invention provides the use of a compound according to any one of the above embodiments for the preparation of a medicament for delaying or preventing disease progression in type 2 diabetes.

In the present specification, the following terms have the indicated meaning:

The term "polypeptide" and "peptide" as used herein means a compound composed of at least five constituent amino acids connected by peptide bonds. The constituent amino acids may be from the group of the amino acids encoded by the genetic code and they may be natural amino acids which are not encoded by the genetic code, as well as synthetic amino acids. Natural amino acids which are not encoded by the genetic code are e.g., γ-carboxyglutamate, ornithine, phosphoserine, D-alanine and D-glutamine. Synthetic amino acids comprise amino acids manufactured by chemical synthesis, i.e. D-isomers of the amino acids encoded by the genetic code such as D-alanine and D-leucine, Aib (α-aminoisobutyric acid), Abu (α-aminobutyric acid), Tle (tert-butylglycine), β-alanine, 3-aminomethyl benzoic acid, anthranilic acid.

The 22 proteogenic amino acids are:

Alanine, Arginine, Asparagine, Aspartic acid, Cysteine, Cystine, Glutamine, Glutamic acid, Glycine, Histidine, Hydroxyproline, Isoleucine, Leucine, Lysine, Methionine, Phenylalanine, Proline, Serine, Threonine, Tryptophan, Tyrosine, Valine.

Thus a non-proteogenic amino acid is a moiety which can be incorporated into a peptide via peptide bonds but is not a proteogenic amino acid. Examples are γ-carboxyglutamate, ornithine, phosphoserine, the D-amino acids such as D-alanine and D-glutamine, Synthetic non-proteogenic amino acids comprise amino acids manufactured by chemical synthesis, i.e.

D-isomers of the amino acids encoded by the genetic code such as D-alanine and D-leucine, Aib (α-aminoisobutyric acid), Abu (α-aminobutyric acid), Tle (tert-butylglycine), 3-aminomethyl benzoic acid, anthranilic acid, des-amino-Histidine, the beta analogues of amino acids such as β-alanine etc. D-histidine, desamino-histidine, 2-amino-histidine, 3-hydroxy-histidine, homohistidine, $N^\alpha$-acetyl-histidine, α-fluoromethyl-histidine, α-methyl-histidine, 3-pyridylalanine, 2-pyridylalanine or 4-pyridylalanine, (1-aminocyclopropyl) carboxylic acid, (1-aminocyclobutyl) carboxylic acid, (1-aminocyclopentyl) carboxylic acid, (1-aminocyclohexyl) carboxylic acid, (1-aminocycloheptyl) carboxylic acid, or (1-aminocyclooctyl) carboxylic acid;

The term "analogue" as used herein referring to a polypeptide means a modified peptide wherein one or more amino acid residues of the peptide have been substituted by other amino acid residues and/or wherein one or more amino acid residues have been deleted from the peptide and/or wherein one or more amino acid residues have been deleted from the peptide and or wherein one or more amino acid residues have been added to the peptide. Such addition or deletion of amino acid residues can take place at the N-terminal of the peptide and/or at the C-terminal of the peptide. A simple system is often used to describe analogues: For example [$Arg^{34}$]exendin-4(1-39)Lys designates an exendin-4(1-39) analogue wherein the naturally occurring Gly at position 34 has been substituted with arginine and wherein a lysine has been added to the terminal amino acid residue, i.e. to the $Ser^{39}$. All amino acids for which the optical isomer is not stated is to be understood to mean the L-isomer. In embodiments of the invention a maximum of 17 amino acids have been modified. In embodiments of the invention a maximum of 15 amino acids have been modified. In embodiments of the invention a maximum of 10 amino acids have been modified. In embodiments of the invention a maximum of 8 amino acids have been modified. In embodiments of the invention a maximum of 7 amino acids have been modified. In embodiments of the invention a maximum of 6 amino acids have been modified. In embodiments of the invention a maximum of 5 amino acids have been modified. In embodiments of the invention a maximum of 4 amino acids have been modified. In embodiments of the invention a maximum of 3 amino acids have been modified. In embodiments of the invention a maximum of 2 amino acids have been modified. In embodiments of the invention 1 amino acid has been modified.

The term "derivative" as used herein in relation to a peptide means a chemically modified peptide or an analogue thereof, wherein at least one substituent is not present in the unmodified peptide or an analogue thereof, i.e. a peptide which has been covalently modified. Typical modifications are amides, carbohydrates, alkyl groups, acyl groups, esters and the like.

The term "insulinotropic agent" as used herein means a compound which is an agonist of the human GLP-1 receptor, i.e. a compound which stimulates the formation of cAMP in a suitable medium containing the human GLP-1 receptor (one such medium disclosed below). The potency of an insulinotropic agent is determined by calculating the $EC_{50}$ value from the dose-response curve as described below.

Baby hamster kidney (BHK) cells expressing the cloned human GLP-1 receptor (BHK-467-12A) were grown in DMEM media with the addition of 100 IU/mL penicillin, 100 µg/mL streptomycin, 5% fetal calf serum and 0.5 mg/mL Geneticin G-418 (Life Technologies). The cells were washed twice in phosphate buffered saline and harvested with Versene. Plasma membranes were prepared from the cells by homogenisation with an Ultraturrax in buffer 1 (20 mM HEPES-Na, 10 mM EDTA, pH 7.4). The homogenate was centrifuged at 48,000×g for 15 min at 4° C. The pellet was suspended by homogenization in buffer 2 (20 mM HEPES-Na, 0.1 mM EDTA, pH 7.4), then centrifuged at 48,000×g for 15 min at 4° C. The washing procedure was repeated one more time. The final pellet was suspended in buffer 2 and used immediately for assays or stored at −80° C.

The functional receptor assay was carried out by measuring cyclic AMP (cAMP) as a response to stimulation by the insulinotropic agent. cAMP formed was quantified by the AlphaScreen™ cAMP Kit (Perkin Elmer Life Sciences). Incubations were carried out in half-area 96-well microtiter plates in a total volume of 50 µL buffer 3 (50 mM Tris-HCl, 5 mM HEPES, 10 mM $MgCl_2$, pH 7.4) and with the following additions: 1 mM ATP, 1 µM GTP, 0.5 mM 3-isobutyl-1-methylxanthine (IBMX), 0.01% Tween-20, 0.1% BSA, 6 µg membrane preparation, 15 µg/mL acceptor beads, 20 µg/mL donor beads preincubated with 6 nM biotinyl-cAMP. Compounds to be tested for agonist activity were dissolved and diluted in buffer 3. GTP was freshly prepared for each experiment. The plate was incubated in the dark with slow agitation for three hours at room temperature followed by counting in the Fusion™ instrument (Perkin Elmer Life Sciences). Concentration-response curves were plotted for the individual compounds and $EC_{50}$ values estimated using a four-parameter logistic model with Prism v. 4.0 (GraphPad, Carlsbad, Calif.).

The term "DPP-IV protected" as used herein referring to a polypeptide means a polypeptide which has been chemically modified in order to render said compound resistant to the plasma peptidase dipeptidyl aminopeptidase-4 (DPP-IV). The DPP-IV enzyme in plasma is known to be involved in the degradation of several peptide hormones, e.g. GLP-1, GLP-2, Exendin-4 etc. Thus, a considerable effort is being made to develop analogues and derivatives of the polypeptides susceptible to DPP-IV mediated hydrolysis in order to reduce the rate of degradation by DPP-IV.

In one embodiment a compound according to the invention is DPP-IV protected. In a further embodiment according to the invention a DPP-IV protected peptide is more resistant to DPP-IV than GLP-1(7-37) or Exendin-4(1-39).

Resistance of a peptide to degradation by dipeptidyl aminopeptidase IV is determined by the following degradation assay:

Aliquots of the peptide (5 nmol) are incubated at 37° C. with 1 µL of purified dipeptidyl aminopeptidase IV corresponding to an enzymatic activity of 5 mU for 10-180 minutes in 100 µL of 0.1 M triethylamine-HCl buffer, pH 7.4. Enzymatic reactions are terminated by the addition of 5 µL of 10% trifluoroacetic acid, and the peptide degradation products are separated and quantified using HPLC analysis. One method for performing this analysis is: The mixtures are applied onto a Vydac C18 widepore (30 nm pores, 5 µm particles) 250×4.6 mm column and eluted at a flow rate of 1 ml/min with linear stepwise gradients of acetonitrile in 0.1% trifluoroacetic acid (0% acetonitrile for 3 min, 0-24% acetonitrile for 17 min, 24-48% acetonitrile for 1 min) according to Siegel et al., Regul. Pept. 1999; 79:93-102 and Mentlein et al. Eur. J. Biochem. 1993; 214:829-35. Peptides and their degradation products may be monitored by their absorbance at 220 nm (peptide bonds) or 280 nm (aromatic amino acids), and are quantified by integration of their peak areas related to those of standards. The rate of hydrolysis of a peptide by dipeptidyl aminopeptidase IV is estimated at incubation times which result in less than 10% of the peptide being hydrolysed.

The term "pharmaceutically acceptable" as used herein means suited for normal pharmaceutical applications, i.e. giving rise to no adverse events in patients etc.

The term "excipient" as used herein means the chemical compounds which are normally added to pharmaceutical compositions, e.g. buffers, tonicity agents, preservatives and the like.

The term "effective amount" as used herein means a dosage which is sufficient to be effective for the treatment of the patient compared with no treatment.

The term "pharmaceutical composition" as used herein means a product comprising an active compound or a salt thereof together with pharmaceutical excipients such as buffer, preservative, and optionally a tonicity modifier and/or a stabilizer. Thus a pharmaceutical composition is also known in the art as a pharmaceutical formulation.

The term "treatment of a disease" as used herein means the management and care of a patient having developed the disease, condition or disorder. The purpose of treatment is to combat the disease, condition or disorder. Treatment includes the administration of the active compounds to eliminate or control the disease, condition or disorder as well as to alleviate the symptoms or complications associated with the disease, condition or disorder.

In another aspect the present invention relates to a derivative of exendin-4 or an analogue thereof that can bind to albumin and the GLP-1 receptor simultaneously.

In another aspect the present invention relates to a derivative of exendin-4 or an analogue thereof that bind to the GLP-1 receptor with an affinity below 100 nM, preferable below 30 nM in the presence of 2% albumin.

In another aspect the present invention relates to a derivative of exendin-4 or an analogue thereof which affinity to the GLP-1 receptor is only partly decreased when comparing the affinity in the presence of very low concentration (e.g. 0.005% to 0.2%) of human albumin to the affinity in the presence of 2% human albumin. The shift in binding affinity under these conditions is less than 50 fold, preferable below 30 fold and more preferable below 10 fold.

In another aspect the present invention relates to a derivative of exendin-4 or an analogue thereof which is stable against the chemical degradation normally seen with exendin-4—especially oxidation and deamidation.

In another aspect the present invention relates to a derivative of exendin-4 or an analogue thereof which has a long in vivo half-life compared to underivatized exendin-4.

In another aspect the present invention relates to a derivative of exendin-4 or an analogue thereof which has a high potency at the receptor. For strong albumin binding analogues, the potency is better than 1000 µM and for less albumin binding analogues, the potency is as low as 50 µM or even more potent (below 10 µM) in the cAMP assay.

In another aspect the present invention relates to a derivative of exendin-4 or an analogue which has substantially improved terminal halflife in a non-rodent model relative to exendin or GLP-1. Preferred is a terminal half-life longer than 5 hours in pigs, monkeys or humans using iv dosing.

In another aspect the present invention relates to a derivative of exendin-4 or an analogue which can be formulated into particles suitable for pulmonary administration In another aspect the present invention relates to a derivative of exendin-4 or an analogue which is chemically and physically stable at neutral pH most preferably in the range 6-8.

In another aspect the present invention relates to a derivative of exendin-4 or an analogue thereof which has little or no tendency to aggregate.

Liquid shelf stable pharmaceutical compositions for injection of derivatives of exendin-4 or analogues can be formulated at neutral pH, such as pH 6-8.5, if susceptible degradation sites in the native exendin-4 peptide is exchanged with more chemical stable residues.

The term "shelf-stable pharmaceutical composition" as used herein means a pharmaceutical composition which is stable for at least the period which is required by regulatory agencies in connection with therapeutic peptides. Preferably, a shelf-stable pharmaceutical composition is stable for at least one year at 5° C. Shelf-stability includes chemical stability as well as physical stability. Chemical instability involves degradation of covalent bonds, such as hydrolysis as in deamidation, racemization, oxidation or crosslinking. Chemical stability of the formulations is evaluated by means of e.g. reverse phase (RP-HPLC), size exclusion chromatography (SE-HPLC), mass spectroscopy and electrophoresis. The susceptible degradation sites of proteins can effectively be detected by peptide mapping and mass spectroscopy. In one aspect of the invention, the formation of peptide related impurities during shelf-life is less than 10% of the total peptide content. In a further aspect of the invention, the formation of peptide related during impurities during shelf-life is less than 5%. Physical instability involves conformational changes relative to the native structure, which includes loss of higher order structure, aggregation, fibrillation, precipitation or adsorption to surfaces. Insulin peptides, GLP-1 compounds and amylin compounds are known to be prone to instability due to fibrillation. Physical stability of the formulations may be evaluated by conventional means of e.g. visual inspection, nephelometry and Thioflavin T assay after storage of the formulation at different temperatures for various time periods. Conformational stability can be evaluated by circular dichroism and NMR as described by e.g. Hudson and Andersen, Peptide Science, vol 76 (4), pp. 298-308 (2004).

In another aspect the present invention relates to a derivative of exendin-4 or an analogue thereof which is suitable for pulmonal delivery. This may be with regard to physical or chemical aspects which are useful for a pulmonal formulation. Alternatively, the compounds are stable against degradation by enzymes in the airways and lungs.

In embodiments of the invention a combination of the above features is achieved.

The term "albumin binding moiety" as used herein means a residue which binds non-covalently to human serum albumin. The albumin binding residue attached to the therapeutic polypeptide typically has an affinity below 10 µM to human serum albumin and preferably below 1 µM. A range of albumin binding residues are known among linear and branched lipohophillic moieties containing 4-40 carbon atoms having a distal acidic group.

The term "hydrophilic linker" as used herein means a spacer that separates a peptide and an albumin binding residue with a chemical moiety which comprises at least 5 non-hydrogen atoms where 30-50% of these are either N or O.

In the formulas below the terminal bonds from the attached groups are to be regarded as attachment bonds and not ending in methylene groups unless stated.

Another object of the present invention is to provide a pharmaceutical formulation comprising a compound according to the present invention which is present in a concentration from 0.1 mg/ml to 25 mg/ml, and wherein said formulation has a pH from 3.0 to 9.0. The formulation may further comprise a buffer system, preservative(s), tonicity agent(s), chelating agent(s), stabilizers and surfactants. In one embodiment of the invention the pharmaceutical formulation is an aqueous formulation, i.e. formulation comprising water. Such formulation is typically a solution or a suspension. In a further embodiment of the invention the pharmaceutical formulation is an aqueous solution. The term "aqueous formulation" is defined as a formulation comprising at least 50% w/w water. Likewise, the term "aqueous solution" is defined as a solution comprising at least 50% w/w water, and the term "aqueous suspension" is defined as a suspension comprising at least 50% w/w water.

In another embodiment the pharmaceutical formulation is a freeze-dried formulation, whereto the physician or the patient adds solvents and/or diluents prior to use.

In another embodiment the pharmaceutical formulation is a dried formulation (e.g. freeze-dried or spray-dried) ready for use without any prior dissolution.

In a further aspect the invention relates to a pharmaceutical formulation comprising an aqueous solution of a compound according to the present invention, and a buffer, wherein said compound is present in a concentration from 0.1 mg/ml or above, and wherein said formulation has a pH from about 3.0 to about 9.0.

In another embodiment of the invention the pH of the formulation is from about 7.0 to about 9.5. In another embodiment of the invention the pH of the formulation is from about 3.0 to about 7.0. In another embodiment of the invention the pH of the formulation is from about 5.0 to about 7.5. In another embodiment of the invention the pH of the formulation is from about 7.5 to about 9.0. In another embodiment of the invention the pH of the formulation is from about 7.5 to about 8.5. In another embodiment of the invention the pH of the formulation is from about 6.0 to about 7.5. In another embodiment of the invention the pH of the formulation is from about 6.0 to about 7.0. In another embodiment the pharmaceutical formulation is from 8.0 to 8.5.

In an embodiment of the invention each administered dose contains from 0.01 mg-10 mg of active compound. In an embodiment the dose administered contains more than 0.05 mg active compound. In an embodiment the dose administered contains more than 0.1 mg active compound. In an embodiment the dose administered contains up to 10 mg active compound. In an embodiment the dose administered contains up to 9 mg active compound.

In an embodiment the dose administered contains up to 8 mg active compound. In an embodiment the dose administered contains up to 7 mg active compound. In an embodiment the dose administered contains up to 6 mg active compound. In an embodiment the dose administered contains up to 5 mg active compound. In an embodiment the dose administered contains from 0.2 mg to 5 mg active compound.

In a further embodiment of the invention the buffer is selected from the group consisting of sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethan, bicine, tricine, malic acid, succinate, maleic acid, fumaric acid, tartaric acid, aspartic acid or mixtures thereof. Each one of these specific buffers constitutes an alternative embodiment of the invention.

In a further embodiment of the invention the formulation further comprises a pharmaceutically acceptable preservative. In a further embodiment of the invention the preservative is selected from the group consisting of phenol, o-cresol, m-cresol, p-cresol, methyl p-hydroxybenzoate, propyl p-hydroxybenzoate, 2-phenoxyethanol, butyl p-hydroxybenzoate, 2-phenylethanol, benzyl alcohol, chlorobutanol, and thiomerosal, bronopol, benzoic acid, imidurea, chlorohexidine, sodium dehydroacetate, chlorocresol, ethyl p-hydroxybenzoate, benzethonium chloride, chlorphenesine (3p-chlorphenoxypropane-1,2-diol) or mixtures thereof. In an embodiment the preservative is phenol or m-cresol. In a further embodiment of the invention the preservative is present in a concentration from 0.1 mg/ml to 20 mg/ml. In a further embodiment of the invention the preservative is present in a concentration from 0.1 mg/ml to 5 mg/ml. In a further embodiment of the invention the preservative is present in a concentration from 5 mg/ml to 10 mg/ml. In a further embodiment of the invention the preservative is present in a concentration from 10 mg/ml to 20 mg/ml. Each one of these specific preservatives constitutes an alternative embodiment of the invention. The use of a preservative in pharmaceutical compositions is well-known to the skilled person. For convenience reference is made to Remington: *The Science and Practice of Pharmacy*, 19$^{th}$ edition, 1995.

In a further embodiment of the invention the formulation further comprises an isotonic agent. In a further embodiment of the invention the isotonic agent is selected from the group consisting of a salt (e.g. sodium chloride), a sugar or sugar alcohol, an amino acid (e.g. L-glycine, L-histidine, arginine, lysine, isoleucine, aspartic acid, tryptophan, threonine), an alditol (e.g. glycerol (glycerine), 1,2-propanediol (propyleneglycol), 1,3-propanediol, 1,3-butanediol)polyethyleneglycol (e.g. PEG400), or mixtures thereof. In an embodiment the isotoncity agent is propyleneglycol. Any sugar such as mono-, di-, or polysaccharides, or water-soluble glucans, including for example fructose, glucose, mannose, sorbose, xylose, maltose, lactose, sucrose, trehalose, dextran, pullulan, dextrin, cyclodextrin, alfa and beta HPCD, soluble starch, hydroxyethyl starch and carboxymethylcellulose-Na may be used. In one embodiment the sugar additive is sucrose. Sugar alcohol is defined as a C4-C8 hydrocarbon having at least one —OH group and includes, for example, mannitol, sorbitol, inositol, galactitol, dulcitol, xylitol, and arabitol. In one embodiment the sugar alcohol additive is mannitol. The sugars or sugar alcohols mentioned above may be used individually or in combination. There is no fixed limit to the amount used, as long as the sugar or sugar alcohol is soluble in the liquid preparation and does not adversely effect the stabilizing effects achieved using the methods of the invention. In one embodiment, the sugar or sugar alcohol concentration is between about 1 mg/ml and about 150 mg/ml. In a further embodiment of the invention the isotonic agent is present in a concentration from 1 mg/ml to 50 mg/ml. In a further embodiment of the invention the isotonic agent is present in a concentration from 1 mg/ml to 7 mg/ml. In an embodiment of the invention the isotonic agent is present in a concentration from 5 mg/ml to 7 mg/ml. In a further embodiment of the invention the isotonic agent is present in a concentration from 8 mg/ml to 24 mg/ml. In a further embodiment of the invention the isotonic agent is present in a concentration from 25 mg/ml to 50 mg/ml. Each one of these specific isotonic agents constitutes an alternative embodiment of the invention. The use of an isotonic agent in pharmaceutical compositions is well-known to the skilled person. For convenience reference is made to Remington: *The Science and Practice of Pharmacy*, 19$^{th}$ edition, 1995.

In a further embodiment of the invention the formulation further comprises a chelating agent. In a further embodiment of the invention the chelating agent is selected from salts of ethylenediaminetetraacetic acid (EDTA), citric acid, and aspartic acid, and mixtures thereof. In a further embodiment of the invention the chelating agent is present in a concentration from 0.1 mg/ml to 5 mg/ml. In a further embodiment of the invention the chelating agent is present in a concentration from 0.1 mg/ml to 2 mg/ml. In a further embodiment of the invention the chelating agent is present in a concentration from 2 mg/ml to 5 mg/ml. Each one of these specific chelating agents constitutes an alternative embodiment of the invention. The use of a chelating agent in pharmaceutical compositions is well-known to the skilled person. For convenience reference is made to Remington: *The Science and Practice of Pharmacy*, 19$^{th}$ edition, 1995.

In a further embodiment of the invention the formulation further comprises a stabilizer. The use of a stabilizer in pharmaceutical compositions is well-known to the skilled person. For convenience reference is made to Remington: *The Science and Practice of Pharmacy*, 19$^{th}$ edition, 1995.

More particularly, compositions of the invention are stabilized liquid pharmaceutical compositions whose therapeutically active components include a polypeptide that possibly exhibits aggregate formation during storage in liquid pharmaceutical formulations. By "aggregate formation" is intended a physical interaction between the polypeptide molecules that results in formation of oligomers, which may remain soluble, or large visible aggregates that precipitate from the solution. By "during storage" is intended a liquid pharmaceutical composition or formulation once prepared, is not immediately administered to a subject. Rather, following preparation, it is packaged for storage, either in a liquid form, in a frozen state, or in a dried form for later reconstitution into a liquid form or other form suitable for administration to a subject. By "dried form" is intended the liquid pharmaceutical composition or formulation is dried either by freeze drying (i.e., lyophilization; see, for example, Williams and Polli (1984) J. Parenteral Sci. Technol. 38:48-59), spray drying (see Masters (1991) in Spray-Drying Handbook (5th ed; Longman Scientific and Technical, Essez, U.K.), pp. 491-676; Broadhead et al. (1992) Drug Devel. Ind. Pharm. 18:1169-1206; and Mumenthaler et al. (1994) Pharm. Res. 11:12-20), or air drying (Carpenter and Crowe (1988) Cryobiology 25:459-470; and Roser (1991) Biopharm. 4:47-53). Aggregate formation by a polypeptide during storage of a liquid pharmaceutical composition can adversely affect biological activity of that polypeptide, resulting in loss of therapeutic efficacy of the pharmaceutical composition. Furthermore, aggregate formation may cause other problems such as blockage of tubing, membranes, or pumps when the polypeptide-containing pharmaceutical composition is administered using an infusion system.

The pharmaceutical compositions of the invention may further comprise an amount of an amino acid base sufficient to decrease aggregate formation by the polypeptide during storage of the composition. By "amino acid base" is intended an amino acid or a combination of amino acids, where any given amino acid is present either in its free base form or in its salt form. Where a combination of amino acids is used, all of the amino acids may be present in their free base forms, all may be present in their salt forms, or some may be present in their free base forms while others are present in their salt forms. In one embodiment, amino acids to use in preparing the compositions of the invention are those carrying a charged side chain, such as arginine, lysine, aspartic acid, and glutamic acid. Any stereoisomer (i.e., L, D, or a mixture thereof) of a particular amino acid (e.g. methionine, histidine, imidazole, arginine, lysine, isoleucine, aspartic acid, tryptophan, threonine and mixtures thereof) or combinations of these stereoisomers, may be present in the pharmaceutical compositions of the invention so long as the particular amino acid is present either in its free base form or its salt form. In one embodiment the L-stereoisomer is used. Compositions of the invention may also be formulated with analogues of these amino acids. By "amino acid analogue" is intended a derivative of the naturally occurring amino acid that brings about the desired effect of decreasing aggregate formation by the polypeptide during storage of the liquid pharmaceutical compositions of the invention. Suitable arginine analogues include, for example, aminoguanidine, ornithine and N-monoethyl L-arginine, suitable methionine analogues include ethionine and buthionine and suitable cysteine analogues include S-methyl-L cysteine. As with the other amino acids, the amino acid analogues are incorporated into the compositions in either their free base form or their salt form. In a further embodiment of the invention the amino acids or amino acid analogues are used in a concentration, which is sufficient to prevent or delay aggregation of the protein.

In a further embodiment of the invention methionine (or other sulphuric amino acids or amino acid analogues) may be added to inhibit oxidation of methionine residues to methionine sulfoxide when the polypeptide acting as the therapeutic agent is a polypeptide comprising at least one methionine residue susceptible to such oxidation. By "inhibit" is intended minimal accumulation of methionine oxidized species over time. Inhibiting methionine oxidation results in greater retention of the polypeptide in its proper molecular form. Any stereoisomer of methionine (L or D) or combinations thereof can be used. The amount to be added should be an amount sufficient to inhibit oxidation of the methionine residues such that the amount of methionine sulfoxide is acceptable to regulatory agencies. Typically, this means that the composition contains no more than about 10% to about 30% methionine sulfoxide.

Generally, this can be achieved by adding methionine such that the ratio of methionine added to methionine residues ranges from about 1:1 to about 1000:1, such as 10:1 to about 100:1.

In a further embodiment of the invention the formulation further comprises a stabilizer selected from the group of high molecular weight polymers or low molecular compounds. In a further embodiment of the invention the stabilizer is selected from polyethylene glycol (e.g. PEG 3350), polyvinyl alcohol (PVA), polyvinylpyrrolidone, carboxy-/hydroxycellulose or derivates thereof (e.g. HPC, HPC-SL, HPC-L and HPMC), cyclodextrins, sulphur-containing substances as monothioglycerol, thioglycolic acid and 2-methylthioethanol, and different salts (e.g. sodium chloride). Each one of these specific stabilizers constitutes an alternative embodiment of the invention.

The pharmaceutical compositions may also comprise additional stabilizing agents, which further enhance stability of a therapeutically active polypeptide therein. Stabilizing agents of particular interest to the present invention include, but are not limited to, methionine and EDTA, which protect the polypeptide against methionine oxidation, and a nonionic surfactant, which protects the polypeptide against aggregation associated with freeze-thawing or mechanical shearing.

In a further embodiment of the invention the formulation further comprises a surfactant. In another embodiment of the invention the pharmaceutical composition comprises two different surfactants. The term "Surfactant" as used herein refers to any molecules or ions that are comprised of a water-soluble (hydrophilic) part, the head, and a fat-soluble (lipophilic) segment. Surfactants accumulate preferably at interfaces, which the hydrophilic part is orientated towards the water (hydrophilic phase) and the lipophilic part towards the oil- or hydrophobic phase (i.e. glass, air, oil etc.). The concentration at which surfactants begin to form micelles is known as the critical micelle concentration or CMC. Furthermore, surfactants lower the surface tension of a liquid. Surfactants are also known as amphipathic compounds. The term "Detergent" is a synonym used for surfactants in general.

Anionic surfactants may be selected from the group of: Chenodeoxycholic acid, Chenodeoxycholic acid sodium salt, Cholic acid, Dehydrocholic acid, Deoxycholic acid, Deoxycholic acid methyl ester, Digitonin, Digitoxigenin, N,N-Dimethyldodecylamine N-oxide, Docusate sodium, Glycochenodeoxycholic acid sodium, Glycocholic acid hydrate, Glycodeoxycholic acid monohydrate, Glycodeoxycholic acid sodium salt, Glycodeoxycholic acid sodium salt, Glycolithocholic acid 3-sulfate disodium salt, Glycolithocholic acid ethyl ester, N-Lauroylsarcosine sodium salt, N-Lauroylsarcosine sodium salt, N-Lauroylsarcosine, N-Lauroylsarcosine, Lithium dodecyl sulfate, Lugol, 1-Octanesulfonic acid sodium salt, 1-Octanesulfonic acid sodium salt, Sodium 1-butanesulfonate, Sodium 1-decanesulfonate, Sodium 1-dodecanesulfonate, Sodium 1-heptanesulfonate, Sodium 1-heptanesulfonate, Sodium 1-nonanesulfonate, Sodium 1-propanesulfonate monohydrate, Sodium 2-bromoethanesulfonate, Sodium cholate hydrate, ox or sheep bile, Sodium cholate hydrate, Sodium choleate, Sodium deoxycholate, Sodium dodecyl sulfate, Sodium dodecyl sulfate, Sodium hexanesulfonate, Sodium octyl sulfate, Sodium pentanesulfonate, Sodium taurocholate, Taurochenodeoxycholic acid sodium salt, Taurodeoxycholic acid sodium salt monohydrate, Taurolithocholic acid 3-sulfate disodium salt, Tauroursodeoxycholic acid sodium salt, Trizma® dodecyl sulfate, DSS (docusate sodium, CAS registry no [577-11-7]), docusate calcium, CAS registry no [128-49-4]), docusate potassium, CAS registry no [7491-09-0]), SDS (sodium dodecyl sulfate or sodium lauryl sulfate), Dodecylphosphocholine (FOS-Choline-12), Decylphosphocholine (FOS-Choline-10), Nonylphosphocholine (FOS-Choline-9), dipalmitoyl phosphatidic acid, sodium caprylate, and/or Ursodeoxycholic acid.

Cationic surfactants may be selected from the group of: Alkyltrimethylammonium bromide Benzalkonium chloride, Benzalkonium chloride, Benzyldimethylhexadecylammonium chloride, Benzyldimethyltetradecylammonium chloride, Benzyltrimethylammonium tetrachloroiodate, Dimethyldioctadecylammonium bromide, Dodecylethyldimethylammonium bromide, Dodecyltrimethylammonium bromide, Dodecyltrimethylammonium bromide, Ethylhexadecyldimethylammonium bromide, Hexadecyltrimethylammonium bromide, Hexadecyltrimethylammonium bromide, Polyoxyethylene(10)-N-tallow-1, 3-diaminopropane, Thonzonium bromide, and/or Trimethyl (tetradecyl)ammonium bromide.

Nonionic surfactants may be selected from the group of: BigCHAP, Bis(polyethylene glycol bis[imidazoyl carbonyl]), block copolymers as polyethyleneoxide/polypropyleneoxide block copolymers such as poloxamers, poloxamer 188 and poloxamer 407, Brij®35, Brij® 56, Brij® 72, Brij® 76, Brij® 92V, Brij® 97, Brij® 58P, Cremophor® EL, Decaethylene glycol monododecyl ether, N-Decanoyl-N-methyl-glucamine, n-Dodecanoyl-N-methylglucamide, alkyl-polyglucosides, ethoxylated castor oil, Heptaethylene glycol monodecyl ether, Heptaethylene glycol monododecyl ether, Heptaethylene glycol monotetradecyl ether, Hexaethylene glycol monododecyl ether, Hexaethylene glycol monohexadecyl ether, Hexaethylene glycol monooctadecyl ether, Hexaethylene glycol monotetradecyl ether, Igepal CA-630, Igepal CA-630, Methyl-6-O—(N-heptylcarbamoyl)-beta-D-glucopyranoside, Nonaethylene glycol monododecyl ether, N-Nonanoyl-N-methylglucamine, N-Nonanoyl-N-methylglucamine, Octaethylene glycol monodecyl ether, Octaethylene glycol monododecyl ether, Octaethylene glycol monohexadecyl ether, Octaethylene glycol monooctadecyl ether, Octaethylene glycol monotetradecyl ether, Octyl-β-D-glucopyranoside, Pentaethylene glycol monodecyl ether, Pentaethylene glycol monododecyl ether, Pentaethylene glycol monohexadecyl ether, Pentaethylene glycol monohexyl ether, Pentaethylene glycol monooctadecyl ether, Pentaethylene glycol monooctyl ether, Polyethylene glycol diglycidyl ether, Polyethylene glycol ether W-1, Polyoxyethylene 10 tridecyl ether, Polyoxyethylene 100 stearate, Polyoxyethylene 20 isohexadecyl ether, Polyoxyethylene 20 oleyl ether, Polyoxyethylene 40 stearate, Polyoxyethylene 50 stearate, Polyoxyethylene 8 stearate, Polyoxyethylene bis(imidazolyl carbonyl), Polyoxyethylene 25 propylene glycol stearate, Saponin from Quillaja bark, Span® 20, Span® 40, Span® 60, Span® 65, Span® 80, Span® 85, Tergitol, Type 15-S-12, Tergitol, Type 15-S-30, Tergitol, Type 15-S-5, Tergitol, Type 15-S-7, Tergitol, Type 15-S-9, Tergitol, Type NP-10, Tergitol, Type NP-4, Tergitol, Type NP-40, Tergitol, Type NP-7, Tergitol, Type NP-9, Tetradecyl-f3-D-maltoside, Tetraethylene glycol monodecyl ether, Tetraethylene glycol monododecyl ether, Tetraethylene glycol monotetradecyl ether, Triethylene glycol monodecyl ether, Triethylene glycol monododecyl ether, Triethylene glycol monohexadecyl ether, Triethylene glycol monooctyl ether, Triethylene glycol monotetradecyl ether, Triton CF-21, Triton CF-32, Triton DF-12, Triton DF-16, Triton GR-5M, Triton QS-15, Triton QS-44, Triton X-100, Triton X-102, Triton X-15, Triton X-151, Triton X-200, Triton X-207, Triton® X-100, Triton® X-114, Triton® X-165 solution, Triton® X-305 solution, Triton® X-405, Triton® X-45, Triton® X-705-70, TWEEN® 20, TWEEN® 40, TWEEN® 60, TWEEN® 6, TWEEN® 65, TWEEN® 80, TWEEN® 81, TWEEN® 85, Tyloxapol, sphingophospholipids (sphingomyelin), and sphingoglycolipids (ceramides, gangliosides), phospholipids, and/or n-Undecyl β-D-glucopyranoside.

Zwitterionic surfactants may be selected from the group of: CHAPS, CHAPSO, 3-(Decyldimethylammonio)propanesulfonate inner salt, 3-(Dodecyldimethylammonio)-propanesulfonate inner salt, 3-(Dodecyldimethylammonio)propanesulfonate inner salt, 3-(N,N-Dimethylmyristylammonio)propanesulfonate, 3-(N,N-Dimethyloctadecylammonio)-propanesulfonate, 3-(N,N-Dimethyloctylammonio)propanesulfonate inner salt, 3-(N,N-Dimethylpalmitylammonio)propanesulfonate, N-alkyl-N,N-dimethylammonio-1-propanesulfonates, 3-cholamido-1-propyldimethylammonio-1-propanesulfonate, Dodecylphosphocholine, myristoyl lysophosphatidylcholine, Zwittergent 3-12 (N-dodecyl-N,N-dimethyl-3-ammonio-1-propanesulfonate), Zwittergent 3-10 (3-(Decyldimethylammonio)-propanesulfonate inner salt), Zwittergent 3-08 (3-(Octyldimethylammonio)pro-panesulfonate), glycerophospholipids (lecithins, kephalins, phosphatidyl serine), glyceroglycolipids (galactopyranoside), alkyl, alkoxyl(alkyl ester), alkoxy(alkyl ether)-derivatives of lysophosphatidyl and phosphatidylcholines, e.g. lauroyl and myristoyl derivatives of lysophosphatidylcholine, dipalmitoylphosphatidylcholine, and modifications of the polar head group, that is cholines, ethanolamines, phosphatidic acid, serines, threonines, glycerol, inositol, lysophosphatidylserine and lysophosphatidylthreonine, acylcarnitines and derivatives, $N^{beta}$-acylated derivatives of lysine, arginine or histidine, or side-chain acylated derivatives of lysine or arginine, $N^{beta}$-acylated derivatives of dipeptides comprising any combination of lysine, arginine or histidine and a neutral or acidic amino acid, $N^{beta}$-acylated derivative of a tripeptide comprising any combination of a neutral amino acid and two charged amino acids, or the surfactant may be selected from the group of imidazoline derivatives, long-chain fatty acids and salts thereof $C_6$-$C_{12}$ (eg. oleic acid and caprylic acid), N-Hexadecyl-N,N-dimethyl-3-ammonio-1-propane-sulfonate, anionic (alkyl-aryl-sulphonates) monovalent surfactants, palmitoyl lysophosphatidyl-L-serine, lysophospholipids (e.g. 1-acyl-sn-glycero-3-phosphate esters of ethanolamine, choline, serine or threonine), or mixtures thereof.

The term "alkyl-polyglucosides" as used herein in relates to an straight or branched $C_{5-20}$-alkyl, -alkenyl or -alkynyl chain which is substituted by one or more glucoside moieties such as maltoside, saccharide etc. Embodiments of these alkyl-polyglucosides include $C_{6-18}$-alkyl-polyglucosides. Specific embodiments of these alkyl-polyglucosides includes the even numbered carbon-chains such as $C_6$, $C_8$, $C_{10}$, $C_{12}$, $C_{14}$, $C_{16}$, $C_{18}$ and $C_{20}$ alkyl chain. Specific embodiments of the glucoside moieties include pyranoside, glucopyranoside, maltoside, maltotrioside and sucrose. In embodiments of the invention less than 6 glucosid moieties are attached to the alkyl group. In embodiments of the invention less than 5 glucosid moieties are attached to the alkyl group. In embodiments of the invention less than 4 glucosid moieties are attached to the alkyl group. In embodiments of the invention less than 3 glucosid moieties are attached to the alkyl group. In embodiments of the invention less than 2 glucosid moieties are attached to the alkyl group. Specific embodiments of alkyl-polyglucosides are alkyl glucosides such n-decyl β-D-glucopyranoside, decyl β-D-maltopyranoside, dodecyl β-D-glucopyranoside, n-dodecyl β-D-maltoside, n-dodecyl β-D-maltoside, n-dodecyl β-D-maltoside, tetradecyl β-D-glucopyranoside, decyl β-D-maltoside, hexadecyl β-D-maltoside, decyl β-D-maltotrioside, dodecyl β-D-maltotrioside, tetradecyl β-D-maltotrioside, hexadecyl β-D-maltotrioside, n-dodecyl-sucrose, n-decyl-sucrose, sucrose monocaprate, sucrose monolaurate, sucrose monomyristate, and sucrose monopalmitate.

The use of a surfactant in pharmaceutical compositions is well-known to the skilled person. For convenience reference is made to Remington: *The Science and Practice of Pharmacy*, 19$^{th}$ edition, 1995.

In a further embodiment of the invention the formulation further comprises protease inhibitors such as EDTA (ethylenediamine tetraacetic acid) and benzamidineHCl, but other commercially available protease inhibitors may also be used. The use of a protease inhibitor is particular useful in pharmaceutical compositions comprising zymogens of proteases in order to inhibit autocatalysis.

It is possible that other ingredients may be present in the peptide pharmaceutical formulation of the present invention. Such additional ingredients may include wetting agents, emulsifiers, antioxidants, bulking agents, tonicity modifiers, chelating agents, metal ions, oleaginous vehicles, proteins (e.g., human serum albumin, gelatine or proteins) and a zwitterion (e.g., an amino acid such as betaine, taurine, arginine, glycine, lysine and histidine). Such additional ingredients, of course, should not adversely affect the overall stability of the pharmaceutical formulation of the present invention.

Pharmaceutical compositions containing a compound according to the present invention may be administered to a patient in need of such treatment at several sites, for example, at topical sites, for example, skin and mucosal sites, at sites which bypass absorption, for example, administration in an artery, in a vein, in the heart, and at sites which involve absorption, for example, administration in the skin, under the skin, in a muscle or in the abdomen. Administration of pharmaceutical compositions according to the invention may be through several routes of administration, for example, lingual, sublingual, buccal, in the mouth, oral, in the stomach and intestine, nasal, pulmonary, for example, through the bronchioles and alveoli or a combination thereof, epidermal, dermal, transdermal, vaginal, rectal, ocular, for examples through the conjunctiva, uretal, and parenteral to patients in need of such a treatment.

Compositions of the current invention may be administered in several dosage forms, for example, as solutions, suspensions, emulsions, microemulsions, multiple emulsion, foams, salves, pastes, plasters, ointments, tablets, coated tablets, chewing gum, rinses, capsules, for example, hard gelatine capsules and soft gelatine capsules, suppositories, rectal capsules, drops, gels, sprays, powder, aerosols, inhalants, eye drops, ophthalmic ointments, ophthalmic rinses, vaginal pessaries, vaginal rings, vaginal ointments, injection solution, in situ transforming solutions, for example in situ gelling, in situ setting, in situ precipitating, in situ crystallization, infusion solution, and implants.

Compositions of the invention may further be compounded in, or attached to, for example through covalent, hydrophobic and electrostatic interactions, a drug carrier, drug delivery system and advanced drug delivery system in order to further enhance stability of the compound of the present invention, increase bioavailability, increase solubility, decrease adverse effects, achieve chronotherapy well known to those skilled in the art, and increase patient compliance or any combination thereof. Examples of carriers, drug delivery systems and advanced drug delivery systems include, but are not limited to, polymers, for example cellulose and derivatives, polysaccharides, for example dextran and derivatives, starch and derivatives, poly(vinyl alcohol), acrylate and methacrylate polymers, polylactic and polyglycolic acid and block co-polymers thereof, polyethylene glycols, carrier proteins, for example albumin, gels, for example, thermogelling systems, for example block co-polymeric systems well known to those skilled in the art, micelles, liposomes, microspheres, nano-particulates, liquid crystals and dispersions thereof, L2 phase and dispersions thereof, well known to those skilled in the art of phase behaviour in lipid-water systems, polymeric micelles, multiple emulsions, self-emulsifying, self-micro-emulsifying, cyclodextrins and derivatives thereof, and dendrimers.

Compositions of the current invention are useful in the formulation of solids, semisolids, powder and solutions for pulmonary administration of compounds of the present invention, using, for example a metered dose inhaler, dry powder inhaler and a nebulizer, all being devices well known to those skilled in the art.

Compositions of the current invention are specifically useful in the formulation of controlled, sustained, protracting, retarded, and slow release drug delivery systems. More specifically, but not limited to, compositions are useful in formulation of parenteral controlled release and sustained release systems (both systems leading to a many-fold reduction in number of administrations), well known to those skilled in the art. Even more preferably, are controlled release and sustained release systems administered subcutaneous. Without limiting the scope of the invention, examples of useful controlled release system and compositions are hydrogels, oleaginous gels, liquid crystals, polymeric micelles, microspheres, nanoparticles, Methods to produce controlled release systems useful for compositions of the current invention include, but are not limited to, crystallization, condensation, co-crystallization, precipitation, co-precipitation, emulsification, dispersion, high pressure homogenisation, encapsulation, spray drying, microencapsulating, coacervation, phase separation, solvent evaporation to produce microspheres, extrusion and supercritical fluid processes. General reference is made to Handbook of Pharmaceutical Controlled Release (Wise, D. L., ed. Marcel Dekker, New York, 2000) and Drug and the Pharmaceutical Sciences vol. 99: Protein Formulation and Delivery (MacNally, E. J., ed. Marcel Dekker, New York, 2000). Parenteral administration may be performed by subcutaneous, intramuscular, intraperitoneal or intravenous injection by means of a syringe, optionally a pen-like syringe. Alternatively, parenteral administration can be performed by means of an infusion pump. A further option is a composition which may be a solution or suspension or a powder for the administration of the compound of the present invention in the form of a nasal or pulmonal liquid or powder spray. As a still further option, the pharmaceutical compositions containing the compound of the invention can also be adapted to transdermal administration, e.g. by needle-free injection or from a patch, optionally an iontophoretic patch, or transmucosal, e.g. buccal, administration.

The compounds of the present invention can be administered via the pulmonary route in a vehicle, as a solution, suspension or dry powder using any of known types of devices suitable for pulmonary drug delivery. Examples of these comprise, but are not limited to, the three general types of aerosol-generating for pulmonary drug delivery, and may include jet or ultrasonic nebulizers, metered-dose inhalers, or dry powder inhalers (Cf. Yu J, Chien Y W. Pulmonary drug delivery: Physiologic and mechanistic aspects. Crit Rev Ther Drug Carr Sys 14(4) (1997) 395-453).

Based on standardised testing methodology, the aerodynamic diameter ($d_a$) of a particle is defined as the geometric equivalent diameter of a reference standard spherical particle of unit density (1 g/cm$^3$). In the simplest case, for spherical particles, $d_a$ is related to a reference diameter (d) as a function of the square root of the density ratio as described by:

Modifications to this relationship occur for non-spherical particles (cf. Edwards D A, Ben-Jebria A, Langer R. Recent advances in pulmonary drug delivery using large, porous inhaled particles. J Appl Physiol 84(2) (1998) 379-385). The terms "MMAD" and "MMEAD" are well-described and known to the art (cf. Edwards D A, Ben-Jebria A, Langer R and represents a measure of the median value of an aerodynamic particle size distribution. Recent advances in pulmonary drug delivery using large, porous inhaled particles. J Appl Physiol 84(2) (1998) 379-385). Mass median aerodynamic diameter (MMAD) and mass median effective aerodynamic diameter (MMEAD) are used inter-changeably, are statistical parameters, and empirically describe the size of aerosol particles in relation to their potential to deposit in the lungs, independent of actual shape, size, or density (cf. Edwards D A, Ben-Jebria A, Langer R. Recent advances in pulmonary drug delivery using large, porous inhaled particles. J Appl Physiol 84(2) (1998) 379-385). MMAD is normally calculated from the measurement made with impactors, an instrument that measures the particle inertial behaviour in air.

In a further embodiment, the formulation could be aerosolized by any known aerosolisation technology, such as nebulisation, to achieve a MMAD of aerosol particles less than 10 μm, more preferably between 1-5 μm, and most preferably between 1-3 μm. The preferred particle size is based on the most effective size for delivery of drug to the deep lung, where protein is optimally absorbed (cf. Edwards D A, Ben-Jebria A, Langer A, Recent advances in pulmonary drug delivery using large, porous inhaled particles. J Appl Physiol 84(2) (1998) 379-385).

Deep lung deposition of the pulmonal formulations comprising the compound of the present invention may optional be further optimized by using modifications of the inhalation techniques, for example, but not limited to: slow inhalation flow (eg. 30 L/min), breath holding and timing of actuation.

The term "stabilized formulation" refers to a formulation with increased physical stability, increased chemical stability or increased physical and chemical stability.

The term "physical stability" of the protein formulation as used herein refers to the tendency of the protein to form biologically inactive and/or insoluble aggregates of the protein as a result of exposure of the protein to thermo-mechanical stresses and/or interaction with interfaces and surfaces that are destabilizing, such as hydrophobic surfaces and interfaces. Physical stability of the aqueous protein formulations is evaluated by means of visual inspection and/or turbidity measurements after exposing the formulation filled in suitable containers (e.g. cartridges or vials) to mechanical/physical stress (e.g. agitation) at different temperatures for various time periods. Visual inspection of the formulations is performed in a sharp focused light with a dark background. The turbidity of the formulation is characterized by a visual score ranking the degree of turbidity for instance on a scale from 0 to 3 (a formulation showing no turbidity corresponds to a visual score 0, and a formulation showing visual turbidity in daylight corresponds to visual score 3). A formulation is classified physical unstable with respect to protein aggregation, when it shows visual turbidity in daylight. Alternatively, the turbidity of the formulation can be evaluated by simple turbidity measurements well-known to the skilled person. Physical stability of the aqueous protein formulations can also be evaluated by using a spectroscopic agent or probe of the conformational status of the protein. The probe is preferably a small molecule that preferentially binds to a non-native conformer of the protein. One example of a small molecular spectroscopic probe of protein structure is Thioflavin T. Thioflavin T is a fluorescent dye that has been widely used for the detection of amyloid fibrils. In the presence of fibrils, and perhaps other protein configurations as well, Thioflavin T gives rise to a new excitation maximum at about 450 nm and enhanced emission at about 482 nm when bound to a fibril protein form. Unbound Thioflavin T is essentially non-fluorescent at the wavelengths.

Other small molecules can be used as probes of the changes in protein structure from native to non-native states. For instance the "hydrophobic patch" probes that bind preferentially to exposed hydrophobic patches of a protein. The hydrophobic patches are generally buried within the tertiary structure of a protein in its native state, but become exposed as a protein begins to unfold or denature. Examples of these small molecular, spectroscopic probes are aromatic, hydrophobic dyes, such as antrhacene, acridine, phenanthroline or the like. Other spectroscopic probes are metal-amino acid complexes, such as cobalt metal complexes of hydrophobic amino acids, such as phenylalanine, leucine, isoleucine, methionine, and valine, or the like.

The term "chemical stability" of the protein formulation as used herein refers to chemical covalent changes in the protein structure leading to formation of chemical degradation products with potential less biological potency and/or potential increased immunogenic properties compared to the native protein structure. Various chemical degradation products can be formed depending on the type and nature of the native protein and the environment to which the protein is exposed. Elimination of chemical degradation can most probably not be completely avoided and increasing amounts of chemical degradation products is often seen during storage and use of the protein formulation as well-known by the person skilled in the art. Most proteins are prone to deamidation, a process in which the side chain amide group in glutaminyl or asparaginyl residues is hydrolysed to form a free carboxylic acid. Other degradations pathways involves formation of high molecular weight transformation products where two or more protein molecules are covalently bound to each other through transamidation and/or disulfide interactions leading to formation of covalently bound dimer, oligomer and polymer degradation products (*Stability of Protein Pharmaceuticals*, Ahern. T. J. & Manning M. C., Plenum Press, New York 1992). Oxidation (of for instance methionine residues) can be mentioned as another variant of chemical degradation. The chemical stability of the protein formulation can be evaluated by measuring the amount of the chemical degradation products at various time-points after exposure to different environmental conditions (the formation of degradation products can often be accelerated by for instance increasing temperature). The amount of each individual degradation product is often determined by separation of the degradation products depending on molecule size and/or charge using various chromatography techniques (e.g. SEC-HPLC and/or RP-HPLC).

Hence, as outlined above, a "stabilized formulation" refers to a formulation with increased physical stability, increased chemical stability or increased physical and chemical stability. In general, a formulation must be stable during use and storage (in compliance with recommended use and storage conditions) until the expiration date is reached.

In one embodiment of the invention the pharmaceutical formulation comprising the compound of the present invention is stable for more than 6 weeks of usage and for more than 3 years of storage.

In another embodiment of the invention the pharmaceutical formulation comprising the compound of the present invention is stable for more than 4 weeks of usage and for more than 3 years of storage.

In a further embodiment of the invention the pharmaceutical formulation comprising the compound of the present invention is stable for more than 4 weeks of usage and for more than two years of storage.

In an even further embodiment of the invention the pharmaceutical formulation comprising the compound of the present invention is stable for more than 2 weeks of usage and for more than two years of storage.

In another aspect the present invention relates to the use of a compound according to the invention for the preparation of a medicament.

In one embodiment a compound according to the invention is used for the preparation of a medicament for the treatment or prevention of hyperglycemia, type 2 diabetes, impaired glucose tolerance, type 1 diabetes, obesity, hypertension, syndrome X, dyslipidemia, cognitive disorders, atheroschlerosis, myocardial infarction, stroke, coronary heart disease and other cardiovascular disorders, inflammatory bowel syndrome, dyspepsia and gastric ulcers.

In another embodiment a compound according to the invention is used for the preparation of a medicament for delaying or preventing disease progression in type 2 diabetes.

In another embodiment a compound according to the invention is used for the preparation of a medicament for decreasing food intake, decreasing β-cell apoptosis, increasing β-cell function and β-cell mass, and/or for restoring glucose sensitivity to β-cells.

The treatment with a compound according to the present invention may also be combined with a second or more pharmacologically active substances, e.g. selected from antidiabetic agents, antiobesity agents, appetite regulating agents, antihypertensive agents, agents for the treatment and/or prevention of complications resulting from or associated with diabetes and agents for the treatment and/or prevention of complications and disorders resulting from or associated with obesity. Examples of these pharmacologically active substances are: Insulin, sulphonylureas, biguanides, meglitinides, glucosidase inhibitors, glucagon antagonists, DPP-IV (dipeptidyl peptidase-IV) inhibitors, inhibitors of hepatic enzymes involved in stimulation of gluconeogenesis and/or glycogenolysis, glucose uptake modulators, compounds modifying the lipid metabolism such as antihyperlipidemic agents as HMG CoA inhibitors (statins), Gastric Inhibitory Polypeptides (GIP analogues), compounds lowering food intake, RXR agonists and agents acting on the ATP-dependent potassium channel of the β-cells; Cholestyramine, colestipol, clofibrate, gemfibrozil, lovastatin, pravastatin, simvastatin, probucol, dextrothyroxine, neteglinide, repaglinide; β-blockers such as alprenolol, atenolol, timolol, pindolol, propranolol and metoprolol, ACE (angiotensin converting enzyme) inhibitors such as benazepril, captopril, enalapril, fosinopril, lisinopril, alatriopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin; CART (cocaine amphetamine regulated transcript) agonists, NPY (neuropeptide Y) antagonists, PYY agonist, PYY2 agonists, PYY4 agonits, mixed PPY2/PYY4 agonists, MC4 (melanocortin 4) agonists, orexin antagonists, TNF (tumor necrosis factor) agonists, CRF (corticotropin releasing factor) agonists, CRF BP (corticotropin releasing factor binding protein) antagonists, urocortin agonists, β3 agonists, MSH (melanocyte-stimulating hormone) agonists, MCH (melanocyte-concentrating hormone) antagonists, CCK (cholecystokinin) agonists, serotonin re-uptake inhibitors, serotonin and noradrenaline re-uptake inhibitors, mixed serotonin and noradrenergic compounds, 5HT (serotonin) agonists, bombesin agonists, galanin antagonists, growth hormone, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, RXR (retinoid X receptor) modulators, TR β agonists; histamine H3 antagonists, Gastric Inhibitory Polypeptide agonists or antagonists (GIP analogues), gastrin and gastrin analogues.

The treatment with a compound according to this invention may also be combined with surgery—a surgery that influence the glucose levels and/or lipid homeostasis such as gastric banding or gastric bypass.

It should be understood that any suitable combination of the compounds according to the invention with one or more of the above-mentioned compounds and optionally one or more further pharmacologically active substances are considered to be within the scope of the present invention.

The present invention is further illustrated by the following examples which, however, are not to be construed as limiting the scope of protection. The features disclosed in the foregoing description and in the following examples may, both separately and in any combination thereof, be material for realizing the invention in diverse forms thereof.

Examples

Abbreviations Used r.t: Room temperature
DIPEA: diisopropylethylamine
H$_2$O: water
CH$_3$CN: acetonitrile
DMF: NN dimethylformamide
HBTU: 2-(1H-Benzotriazol-1-yl-)-1,1,3,3 tetramethyluronium hexafluorophosphate
Fmoc: 9 H-fluoren-9-ylmethoxycarbonyl
Boc: tert butyloxycarbonyl
OtBu: tert butyl ester
tBu: tert butyl
Trt: triphenylmethyl
Pmc: 2,2,5,7,8-Pentamethyl-chroman-6-sulfonyl
Dde: 1-(4,4-Dimethyl-2,6-dioxocyclohexylidene)ethyl
ivDde: 1-(4,4-Dimethyl-2,6-dioxocyclohexylidene)-3-methylbutyl
Mtt: 4-methyltrityl
Mmt: 4-methoxytrityl
DCM: dichloromethane
TIS: triisopropylsilane)
TFA: trifluoroacetic acid
Et$_2$O: diethylether
NMP: 1-Methyl-pyrrolidin-2-one
DIPEA: Diisopropylethylamine
HOAt: 1-Hydroxy-7-azabenzotriazole
HOBt: 1-Hydroxybenzotriazole
DIC: Diisopropylcarbodiimide A: Synthesis of Resin Bound Peptide.

The protected peptidyl resin was synthesized according to the Fmoc strategy on an Applied Biosystems 433 peptide synthesizer in 0.25 mmol or 1.0 mmol scale using the manufacturer supplied FastMoc UV protocols which employ HBTU (2-(1H-Benzotriazol-1-yl-)-1,1,3,3 tetramethyluronium hexafluorophosphate) or HATU (O-(7-azabenzotriazol-1-yl)-1,1,3,3-tetramethyluronium hexafluorophosphate) mediated couplings in NMP (N-methyl pyrrolidone), and UV monitoring of the deprotection of the Fmoc protection group. The starting resin used for the synthesis of the peptide amides was Rink-Amide resin and either Wang or chlorotrityl resin was used for peptides with a carboxy C-terminal. The protected amino acid derivatives used were standard Fmoc-amino acids (supplied from e.g. Anaspec, or Novabiochem) supplied in preweighed cartridges suitable for the AB1433A synthesizer with the exception of unnatural aminoacids such as Fmoc-Aib-OH (Fmoc-aminoisobutyric acid). The N terminal amino acid was Boc protected at the alpha amino group (e.g. Boc-His(Boc)OH was used for peptides with His at the N-terminal). The epsilon amino group of lysine in position 26 was either protected with Mtt, Mmt, Dde, ivDde, or Boc, depending on the route for attachment of the albumin binding moiety and spacer. The synthesis of the peptides may in some cases be improved by the use of dipeptides protected on the dipeptide amide bond with a group that can be cleaved under acidic conditions such but not limited to 2-Fmoc-oxy-4-methoxybenzyl or 2,4,6-trimethoxybenzyl. In cases where a serine or a threonine is present in the peptide, the use of pseudoproline dipeptides may be used (see e.g. catalogue from Novobiochem 2002/2003 or newer version, or W. R. Sampson (1999), J. Pep. Sci. 5, 403.

Procedure for Removal of ivDde or Dde-Protection.

The resin (0.25 mmol) was placed in a manual shaker/filtration apparatus and treated with 2% hydrazine in N-methyl pyrrolidone (20 ml, 2×12 min) to remove the Dde or ivDde group and wash with N-methyl pyrrolidone (4×20 ml).

Procedure for Removal of Mtt or Mmt-Protection.

The resin (0.25 mmol) was placed in a manual shaker/filtration apparatus and treated with 2% TFA and 2-3% TIS in DCM (20 ml, 5-10 min repeated 6-12 times) to remove the Mtt or Mmt group and wash with DCM (2×20 ml), 10% MeOH and 5% DIPEA in DCM (2×20 ml) and N-methyl pyrrolidone (4×20 ml).

Procedure for Attachment of Sidechains to Lysine Residue.

The albumin binding residue (B—U— sidechain of formula I) can be attached to the peptide either by acylation to resin bound peptide or acylation in solution to the unprotected peptide using standard acylating reagent such as but not limited to DIC, HOBt/DIC, HOAt/DIC, or HBTU.

Attachment to Resin Bound Peptide:

Route I

Activated (active ester or symmetric anhydride) albumin binding residue (A-B)— sidechain of formula I) such as octadecanedioic acid mono-(2,5-dioxo-pyrrolidin-1-yl) ester (Ebashi et al. EP511600, 4 molar equivalents relative to resin bound peptide) was dissolved in NMP (25 mL), added to the resin and shaken overnight at room temperature. The reaction mixture was filtered and the resin was washed extensively with NMP, dichloromethane, 2-propanol, methanol and diethyl ether.

Route II

The albumin binding residue (A-(B)— sidechain of formula I) was dissolved in N-methyl pyrrolidone/methylene chloride (1:1, 10 ml). The activating reagent such as hydroxybenzotriazole (HOBt) (4 molar equivalents relative to resin) and diisopropylcarbodiimide (4 molar equivalents relative to resin) was added and the solution was stirred for 15 min. The solution was added to the resin and diisopropyethylamine (4 molar equivalents relative to resin) was added. The resin was shaken 2 to 24 hours at room temperature. The resin was washed with N-methyl pyrrolidone (2×20 ml), N-methyl pyrrolidone/Methylene chloride (1:1) (2×20 ml) and methylene chloride (2×20 ml).

Route III

Activated (active ester or symmetric anhydride) albumin binding residue (A-B— sidechain of formula I) such as octadecanedioic acid mono-(2,5-dioxo-pyrrolidin-1-yl) ester (Ebashi et al. EP511600, 1-1.5 molar equivalents relative to the peptide was dissolved in an organic solvent such as acetonitrile, THF, DMF, DMSO or in a mixture of water/organic solvent (1-2 ml) and added to a solution of the peptide in water (10-20 ml) together with 10 molar equivalents of DIPEA. In case of protecting groups on the albumin binding residue such as tert.-butyl, the reaction mixture was lyophilized 0/N and the isolated crude peptide deprotected afterwards—in case of a tert-butyl group the peptide was dissolved in a mixture of trifluoroacetic acid, water and triisopropylsilane (90:5:5). After for 30 min the mixture was, evaporated in vacuo and the finale peptide purified by preparative HPLC.

Procedure for Removal of Fmoc-Protection:

The resin (0.25 mmol) was placed in a filter flask in a manual shaking apparatus and treated with N-methyl pyrrolidone/methylene chloride (1:1) (2×20 ml) and with N-methyl pyrrolidone (1×20 ml), a solution of 20% piperidine in N-methyl pyrrolidone (3×20 ml, 10 min each). The resin was washed with N-methyl pyrrolidone (2×20 ml), N-methyl pyrrolidone/Methylene chloride (1:1) (2×20 ml) and methylene chloride (2×20 ml).

Procedure for Cleaving the Peptide Off the Resin:

The peptide was cleaved from the resin by stirring for 180 min at room temperature with a mixture of trifluoroacetic acid, water and triisopropylsilane (95:2.5:2.5 to 92:4:4). The cleavage mixture was filtered and the filtrate was concentrated to an oil by a stream of nitrogen. The crude peptide was precipitated from this oil with 45 ml diethyl ether and washed 1 to 3 times with 45 ml diethyl ether.

Purification:

The crude peptide was purified by semipreparative HPLC on a 20 mm×250 mm column packed with either 5μ, or 7μ, C-18 silica. Depending on the peptide one or two purification systems were used.

TFA: After drying the crude peptide was dissolved in 5 ml 50% acetic acid $H_2O$ and diluted to 20 ml with $H_2O$ and injected on the column which then was eluted with a gradient of 40-60% $CH_3CN$ in 0.1% TFA 10 ml/min during 50 min at 40° C. The peptide containing fractions were collected. The purified peptide was lyophilized after dilution of the eluate with water.

Ammonium sulphate: The column was equilibrated with 40% $CH_3CN$ in 0.05M $(NH_4)_2SO_4$, which was adjusted to pH 2.5 with concentrated $H_2SO_4$. After drying the crude peptide was dissolved in 5 ml 50% acetic acid $H_2O$ and diluted to 20 ml with $H_2O$ and injected on the column which then was eluted with a gradient of 40%-60% $CH_3CN$ in 0.05M $(NH_4)_2SO_4$, pH 2.5 at 10 ml/min during 50 min at 40° C. The peptide containing fractions were collected and diluted with 3 volumes of $H_2O$ and passed through a Sep-Pak® C18 cartridge (Waters part. #:51910) which has been equilibrated with 0.1% TFA. It was then eluted with 70% $CH_3CN$ containing 0.1% TFA and the purified peptide was isolated by lyophilisation after dilution of the eluate with water.

The final product obtained was characterised by analytical RP-HPLC (retention time) and by LCMS The RP-HPLC analysis was performed using UV detection at 214 nm and e.g. a Vydac 218TP54 4.6 mm×250 mm 5μ, C-18 silica column (The Separations Group, Hesperia, USA) and eluted at e.g. 1 ml/min at 42° C. Most often one of four different elution conditions was used:

A1: Equilibration of the column with a buffer consisting of 0.1M $(NH_4)_2SO_4$, which was adjusted to pH 2.5 with concentrated $H_2SO_4$ and elution by a gradient of 0% to 60% $CH_3CN$ in the same buffer during 50 min.

B1: Equilibration of the column with 0.1% TFA/$H_2O$ and elution by a gradient of 0% $CH_3CN$/0.1% TFA/$H_2O$ to 60% $CH_3CN$/0.1% TFA/$H_2O$ during 50 min.

B6: Equilibration of the column with 0.1% TFA/$H_2O$ and elution by a gradient of 0% $CH_3CN$/0.1% TFA/$H_2O$ to 90% $CH_3CN$/0.1% TFA/$H_2O$ during 50 min.

Alternatively the RP-HPLC analysis was performed using UV detection at 214 nm and a Symmetry300, 3.6 mm×150 mm, 3.5μ, C-18 silica column (Waters) which was eluted at 1 ml/min at 42° C.

B4: Equilibration of the column with 0.05% TFA/$H_2O$ and elution by a gradient of 5% $CH_3CN$/0.05% TFA/$H_2O$ to 95% $CH_3CN$/0.05% TFA/$H_2O$ during 15 min.

Alternatively a preparative gradient elution was performed as indicated above and the percentage of acetonitrile where the compound eluted was noted. Identity was confirmed by MALDI.

The following instrumentation was used:

LCMS was performed on a setup consisting of Sciex API 100 Single quadropole mass spectrometer, Perkin Elmer Series 200 Quard pump, Perkin Elmer Series 200 autosampler, Applied Biosystems 785A UV detector, Sedex 75 evaporative light scattering detector.

The instrument control and data acquisition were done by the Sciex Sample control software running on a Windows 2000 computer.

The HPLC pump was connected to two eluent reservoirs containing:
A: 0.05% Trifluoro acetic acid in water
B: 0.05% Trifluoro acetic acid in acetonitrile The analysis was performed at room temperature by injecting an appropriate volume of the sample (preferably 20 µl) onto the column which was eluted with a gradient of acetonitrile.

The HPLC conditions, detector settings and mass spectrometer settings used are given in the following table.

Column: Waters Xterra MS C-18×3 mm id 5 µm
Gradient: 5%-90% acetonitrile linear during 7.5 min at 1.5 ml/min
Detection: 210 nm (analogue output from DAD)
ELS (analogue output from ELS), 40° C.
MS ionisation mode API-ES Alternatively LCMS was performed on a setup consisting of Hewlett Packard series 1100 G1312A Bin Pump, Hewlett Packard series 1100 Column compartment, Hewlett Packard series 1100 G1315A DAD diode array detector, Hewlett Packard series 1100 MSD and Sedere 75 Evaporative Light Scattering detectorcontrolled by HP Chemstation software. The HPLC pump was connected to two eluent reservoirs containing:
A: 10 mM $NH_4OH$ in water
B: 10 mM $NH_4OH$ in 90% acetonitrile The analysis was performed at 23° C. by injecting an appropriate volume of the sample (preferably 20 µl) onto the column which is eluted with a gradient of A and B.

The HPLC conditions, detector settings and mass spectrometer settings used are given in the following table.

Column Waters Xterra MS C-18×3 mm id 5 µm
Gradient 5%-100% acetonitrile linear during 6.5 min at 1.5 ml/min
Detection 210 nm (analogue output from DAD) ELS (analogue output from ELS)
MS ionisation mode API-ES. Scan 100-1000 amu step 0.1 amu According to the procedure above, the following compounds were prepared as non-limiting examples of the invention:

| Molecule example no. | Data |
|---|---|
| Example 1 | HPLC (method B6): RT = 36.024 min LCMS: m/z = 1214.6 $(M + 4H)^{4+}$ Calculated $(M + H)^+ =$ 4854.5 |

N-$\epsilon^{27}$-[2-(2-[2-(2-[2-(2-[4-hexadecanoylamino-4(S)-carboxybutyrylamino]ethoxy)ethoxy]acetylamino)ethoxy]ethoxy)acetyl][Arg$^{12}$,Leu$^{14}$,Lys$^{27}$]Exendin-4(1-39)amide

| | |
|---|---|
| Example 2 | HPLC (method B6): RT = 39.74 min LCMS: m/z = 1652.1 $(M + 3H)^{3+}$ Calculated $(M + H)^+ =$ 4954.7 |

N-$\epsilon^{32}$-(2-(2-(2-(2-(2-(2-(2-(2-(Octadecanoylamino)ethoxy)ethoxy)acetylamino)ethoxy)ethoxy)acetylamino)ethoxy)ethoxy)acetyl))[Arg$^{12}$,Leu$^{14}$,Val$^{27}$,Arg$^{28}$,Lys$^{32}$]Exendin-4(1-39)amide

| Molecule example no. | Data |
|---|---|
| Example 3<br><br>N-ε[28]-(2-(2-(2-(2-(2-(2-(2-(2-(Octadecanoylamino)ethoxy)ethoxy)acetylamino)ethoxy)ethoxy)acetyl-amino)ethoxy)ethoxy)acetyl))[Arg[12],Leu[14],Val[27],Lys[28] Exendin-4(1-39)amide | HPLC (method B6): RT = 39.84 min<br>LCMS: m/z = 1628.8 $(M + 3H)^{3+}$<br>Calculated $(M + H)^+$ = 4870.6 |
| Example 4<br><br>N-ε[20]-[2-(2-[2-(2-[2-(2-[4-hexadecanoylamino-4(S)-carboxybutyrylamino]ethoxy)ethoxy]acetylamino)ethoxy]ethoxy)acetyl][Arg[12,27,28],Leu[14],Lys[20]]Exendin-4(1-39)amide | HPLC (method A1): RT = 45.687 min<br>HPLC (method B6): RT = 34.955 min<br>LCMS: m/z = 1633 $(M + 3H)^{3+}$<br>Calculated $(M + H)^+$ = 4897.6 |
| Example 5<br><br>N-ε[20]-(2-(2-(2-(2-(2-(2-(2-(2-(Octadecanoylamino)ethoxy)ethoxy)acetylamino)ethoxy)ethoxy)acetyl-amino)ethoxy)ethoxy)acety))[Arg[12,27,28],Leu[14],Lys[20] Exendin-4(1-39)amide | HPLC (method B1): RT = 48.741 min<br>HPLC (method B6): RT = 37.488 min<br>LCMS: m/z = 1648 $(M + 3H)^{3+}$<br>Calculated $(M + H)^+$ = 4941.7 |

-continued

| Molecule example no. | Data |
|---|---|

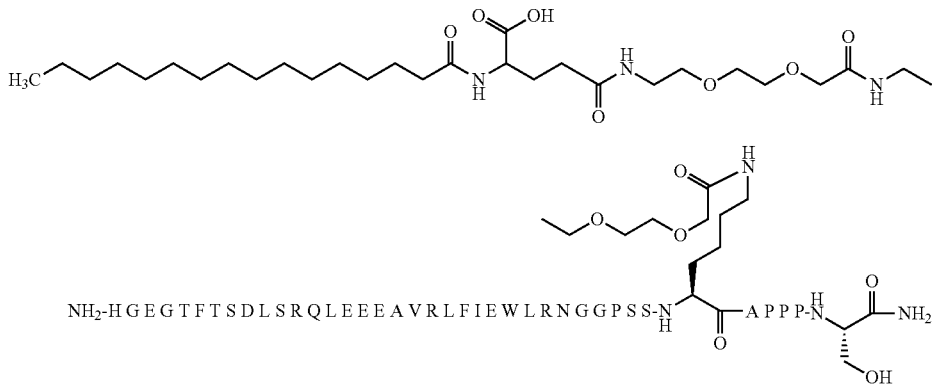

Example 6

N-ε³⁴-[2-(2-[2-(2-[2-(2-[4-hexadecanoylamino-4(S)-
carboxybutyrylamino]ethoxy]ethoxy]acetylamino)ethoxy]ethoxy)acetyl]
[Arg¹²,²⁷,Leu¹⁴,Lys³⁴]Exendin-4(1-39)amide HPLC (method A1): RT = 46.83 min
HPLC (method B6): RT = 35.68 min
LCMS: m/z = 1239.6 (M + 4H)⁴⁺
Calculated (M + H)⁺ = 4953.6

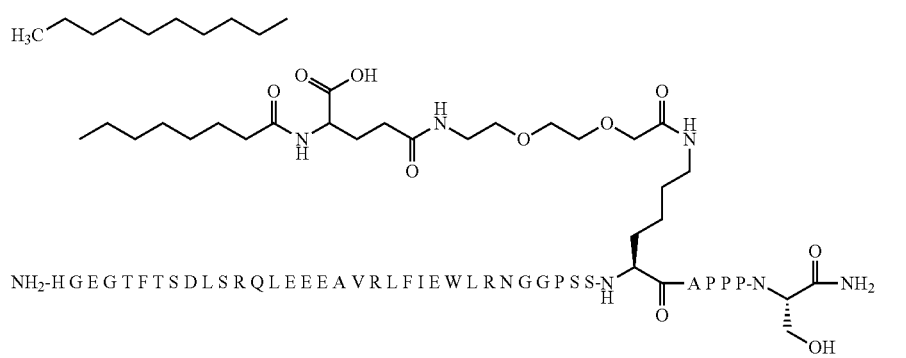

Example 7

N-ε³⁴-[2-(2-[2-[4-hexadecanoylamino-4(S)-
carboxybutyrylamino]ethoxy]ethoxy)acetyl][Arg¹²,²⁷,Leu¹⁴,Lys³⁴]
Exendin-4(1-39)amide HPLC (method A1): RT = 47.20 min
HPLC (method B6): RT = 35.896 min
LCMS: m/z = 1203.2 (M + 4H)⁴⁺
Calculated (M + H)⁺ = 4808.5

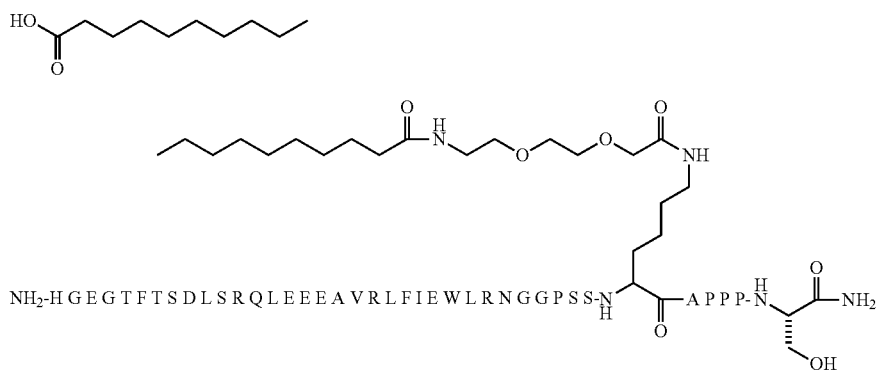

Example 8

N-ε³⁴-(2-(2-(2-(17-carboxyheptadecanoylamino)ethoxy)ethoxy)acetyl)
[Leu¹⁴,Arg¹²,²⁷,Lys³⁴]Exendin-4(1-39)amide HPLC (method A1): RT = 44.74min
HPLC (method B6): RT = 33.71 min
LCMS: m/z = 1185.6 (M + 4H)⁴⁺
Calculated (M + H)⁺ = 4737.4

| Molecule example no. | Data |
|---|---|
| 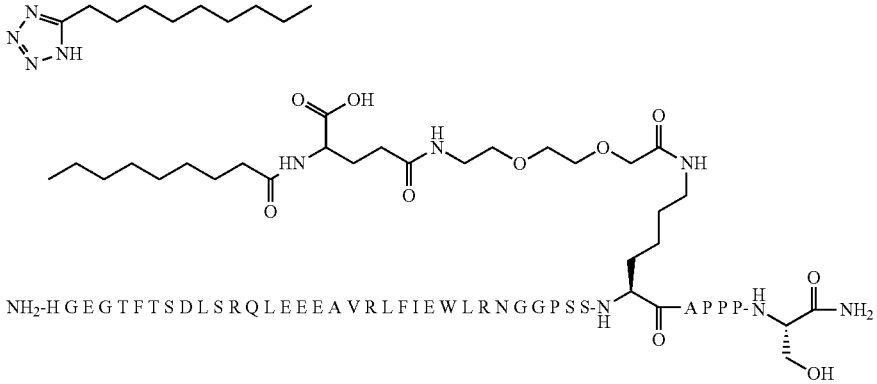 Example 9  N-ε³⁴-(2-(2-(2-(16-tetrazoylhexadecanoylamino-4(S)-carboxybutyrylamino)ethoxy)ethoxy(acetyl)[Leu¹⁴,Arg¹²,²⁷, Lys³⁴]Exendin-4(1-39)amide | HPLC (method A1): RT = 41.88 min HPLC (method B6): RT = 31.64 min LCMS: m/z = 1220.1 $(M + 4H)^{4+}$ Calculated $(M + H)^+$ = 4876.5 |
| 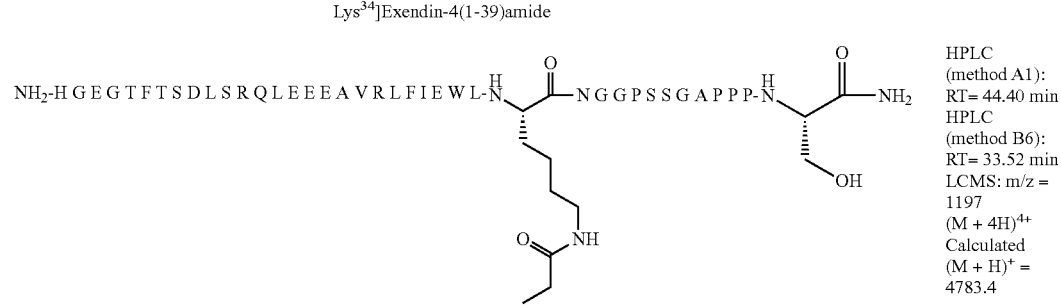 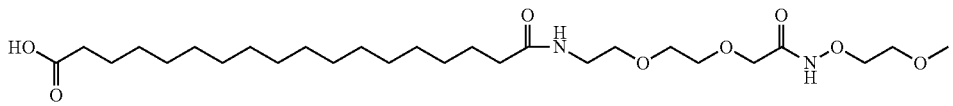 Example 10  N-ε²⁷-(2-(2-(2-(2-(2-(17-carboxyheptadecanoylamino)ethoxy)ethoxy)acetylamino)ethoxy) ethoxy)acetyl][Leu¹⁴,Arg¹²,Lys²⁷]Exendin-4(1-39)amide | HPLC (method A1): RT= 44.40 min HPLC (method B6): RT= 33.52 min LCMS: m/z = 1197 $(M + 4H)^{4+}$ Calculated $(M + H)^+$ = 4783.4 |
| 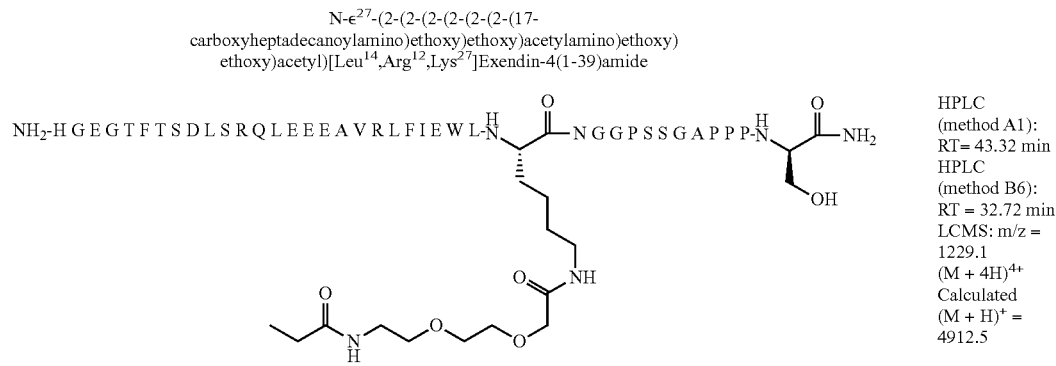 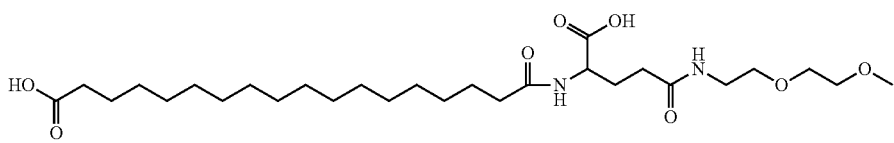 Example 11  N-ε²⁷-(2-(2-(2-(2-(2-(17-carboxyheptadecanoylamino-4(S)-carboxybutyrylamino])ethoxy)ethoxy)acetylamino)ethoxy)ethoxy) acetyl][Leu¹⁴,Arg¹²,Lys²⁷]Exendin-4(1-39)amide | HPLC (method A1): RT = 43.32 min HPLC (method B6): RT = 32.72 min LCMS: m/z = 1229.1 $(M + 4H)^{4+}$ Calculated $(M + H)^+$ = 4912.5 |

-continued

| Molecule example no. | Data |
|---|---|
| 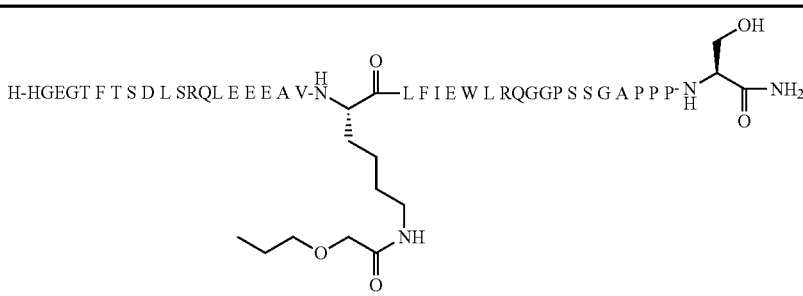 | HPLC (method): B6<br>RT = 33.34 min<br>LCMS: m/z = 1600.1<br>$(M + 3H)^{3+}$<br>Calculated $(M + H)^+$ = 4801 |

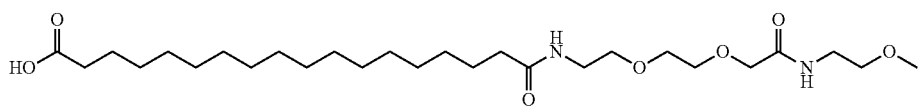

Example 12

N-$\epsilon^{20}$-(2-(2-(2-(2-(2-(17-carboxyheptadecanoylamino)ethoxy)ethoxy)acetylamino)ethoxy)ethoxy)acetyl)[Arg12,Leu14,Arg27,Gln28,Lys20]Exendin-4 (1-39)amide

| | HPLC (method B6):<br>RT = 42.41 min<br>LCMS: m/z = 1661.2<br>$(M + 3H)^{3+}$<br>Calculated $(M + H)^+$ = 4982.8 |
|---|---|

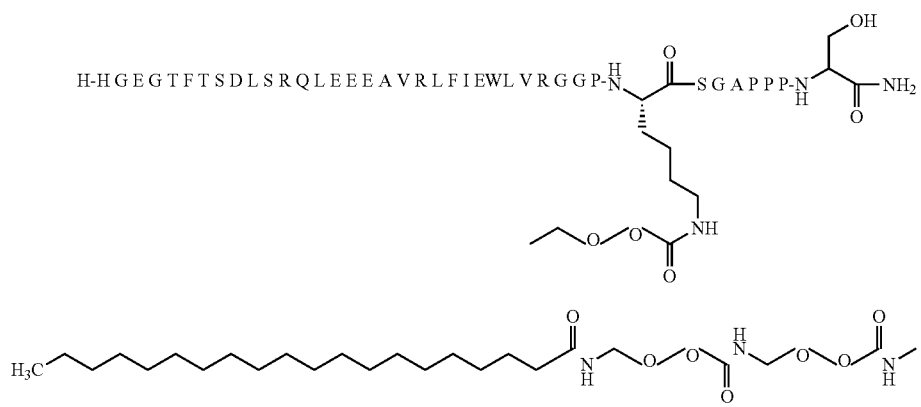

Example 13

N-$\epsilon^{32}$-[2-(2-[2-(2-[2-(2-[2-(2-[2-(Eicosanoylamino)ethoxy]ethoxy)acetylamino]ethoxy)ethoxy]acetylamino)ethoxy]ethoxy)acetyl][Arg12,28,Leu14,Val27,Lys32] Exendin-4-(1-39)amide

| | HPLC (method B6):<br>RT = 38.301 min<br>LCMS: m/z = 1638<br>$(M + 3H)^{3+}$<br>Calculated $(M + H)^+$ = 4913.6 |
|---|---|

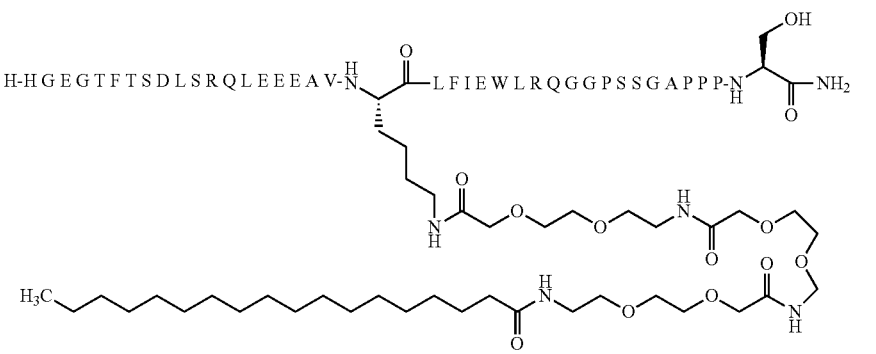

Example 14

N-$\epsilon^{20}$-(2-(2-(2-(2-(2-(2-(2-(2-(Octadecanoylamino)ethoxy)ethoxy)acetylamino)ethoxy)ethoxy)acetylamino)ethoxy)ethoxy)acetyl))[Arg12,27,Gln28,Leu14,Lys20 Exendin-4(1-39)amide

| Molecule example no. | Data |
|---|---|
| 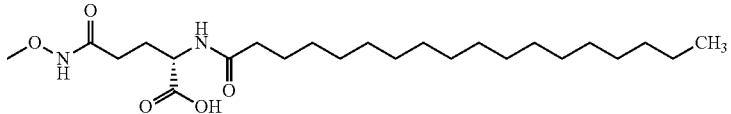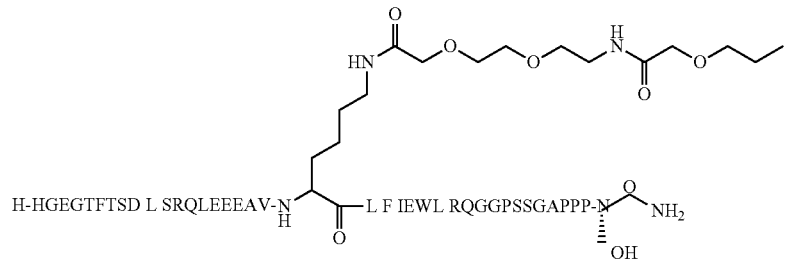

Example 15

N-ε20-[2-(2-[2-(2-[2-(4-Octadecanoylamino-4(S)-carboxybutyrylamino]ethoxy)ethoxy]acetylamino)ethoxy]ethoxy)acetyl][Arg12,27,Gln28,Leu14,Lys20 Exendin-4(1-39)amide | HPLC (method): 03_B6_1<br>RT = 37.553 min<br>LCMS: m/z = 1633.1<br>(M + 3H)3+<br>Calculated (M + H)+ = 4896.6 |
| 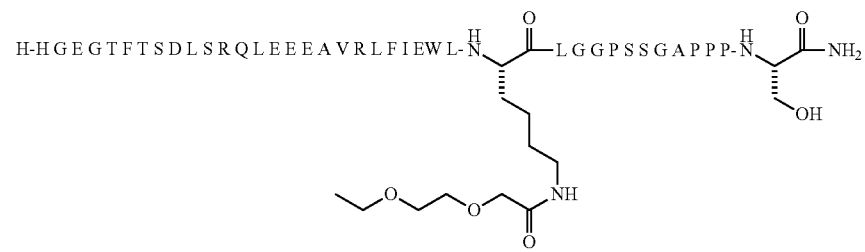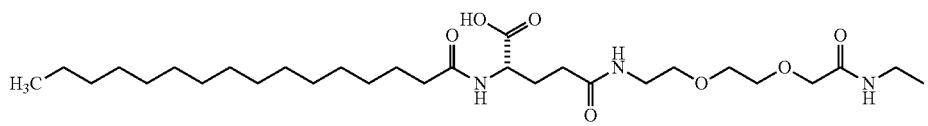

Example 16

N-ε27-2-(2-2-(2-(2-(4-(Hexadecanoylamino)-4(S)-carboxybutyrylamino)ethoxy)ethoxy)acetylamino)ethoxy)ethoxy)acetyl[Arg12,Leu14,Lys27,Leu28]Exendin-4-(1-39)-peptide amide | HPLC (method): B4<br>RT = 12.24 min<br>LCMS: m/z = 1618.8<br>(M + 3H)3+<br>Calculated (M + H)+ = 4853.5 |
| 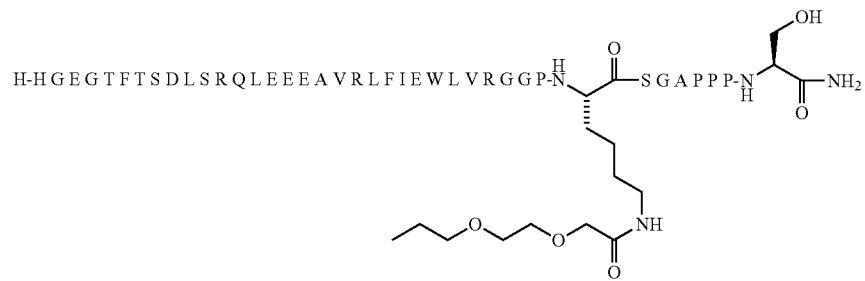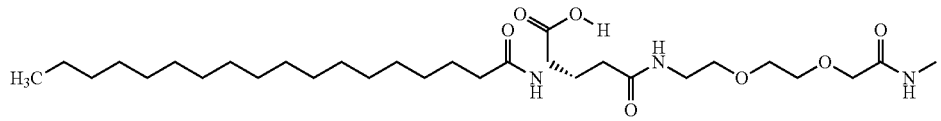

Example 17

N-ε32-(2-(2-(2-(2-(2-(4-(Octadecanoylamino)-4(S)-carboxybutyrylamino))ethoxy)ethoxy)acetylamino)ethoxy)ethoxy)acetyl[Arg12,Leu14,Val27,Arg28,Lys32]Exendin-4-(1-39)amide | HPLC (method B6):<br>RT = 38.82 min<br>LCMS: m/z = 1646.8<br>(M + 3H)3+<br>Calculated (M + H)+ = 4938.7 |

| Molecule example no. | Data |
|---|---|
| 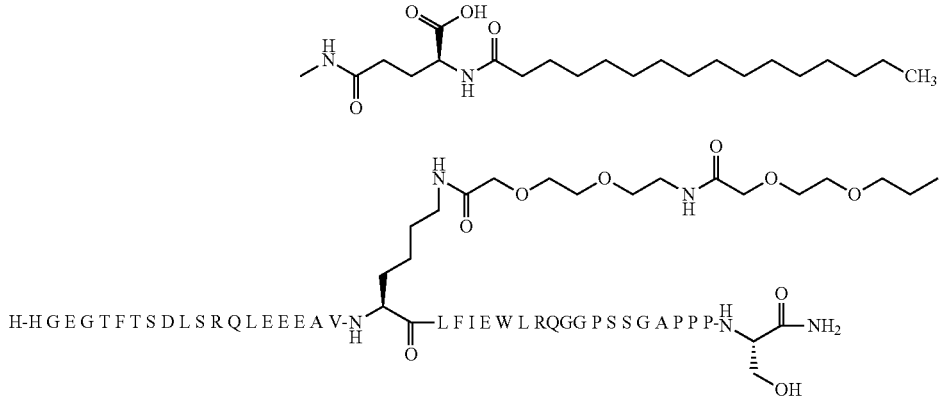

Example 18

N-ε[20]-2-(2-(2-(2-(2-(2-(4-(Hexadecanoylamino)-4(S)-carboxybutyrylamino)ethoxy)ethoxy)acetylamino)ethoxy)ethoxy)acetyl[Arg[12,27],Leu[14],Lys[20],Gln[28]]Exendin-4-(1-39)-peptide amide | HPLC (method B4): RT = 11.938 min LCMS: m/z = 1623.8 (M + 3H)[3+] Calculated (M + H)[+] = 4868.5 |
| 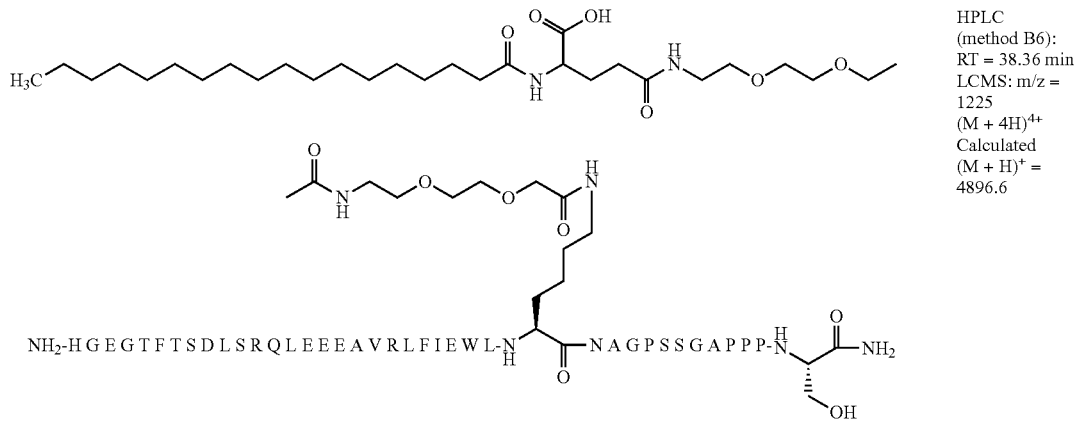

Example 19

N-ε[27]-2-(2-(2-(2-(2-(2-(4-(Octadecanoylamino)-4(S)-carboxybutyrylamino)ethoxy)ethoxy)acetylamino)ethoxy)ethoxy)acetyl[Arg[12],Leu[14],Lys[27],Ala[29]]Exendin-4-(1-39)-amide | HPLC (method B6): RT = 38.36 min LCMS: m/z = 1225 (M + 4H)[4+] Calculated (M + H)[+] = 4896.6 |

| Molecule example no. | Data |
|---|---|

Example 20

N-ε²⁷-(2-(2-(2-(2-(2-(2-(2-(2-(2-(2-(Octadecanoylamino)ethoxy)ethoxy)acetylamino)ethoxy)ethoxy)acetylamino)ethoxy)ethoxy)acetyl)[Arg¹², Leu¹⁴, Lys²⁷, Ala²⁹]Exendin-4-(1-39)-amide HPLC (method B6): 03_B6_1
RT= 39.06 min
LCMS: m/z = 1229.4 (M + 4H)⁴⁺
Calculated (M + H)⁺ = 4912.6

Example 21

N-ε²⁷-{2-(2-(2-(2-[2-(2-(4-(hexadecanoylamino)-4(S)-carboxybutyrylamino)ethoxy)ethoxy)acetylamino)ethoxy)ethoxy)acetyl}[Leu¹⁴,²⁸, Lys²⁷]Exendin-4(1-39)amide RP-HPLC elution at 54.0% acetonitrile
Mass confirmed by MALDI Example 22

N-ε²⁷-(2-(2-(2-(2-(2-(2-(2-(2-(octadecanoylamino)ethoxy)ethoxy)acetylamino)ethoxy)ethoxy)acetylamino)ethoxy)ethoxy)acetyl)[Leu¹⁴,²⁸, Lys²⁷]Exendin-4(1-39)amide RP-HPLC elution at 58.0% acetonitrile
Mass confirmed by MALDI

| Molecule example no. | Data |
|---|---|
| 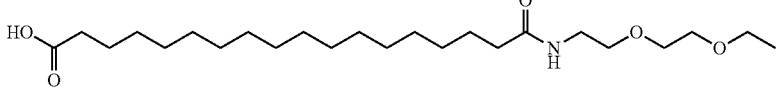<br>Example 23<br><br>N-ε²⁷-(2-(2-(2-(2-(2-(2-(17-carboxyheptadecanoylamino)ethoxy)ethoxy)acetylamino)ethoxy)ethoxy)acetyl)[Leu¹⁴,²⁸,Lys²⁷]Exendin-4(1-39)amide | RP-HPLC elution at 50.7% acetonitrile<br>Mass confirmed by MALDI |
| 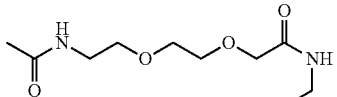<br>Example 24<br><br>N-ε²⁷-(2-(2-(2-(2-(2-(2-(4-(octadecanoylamino)-4(S)-carboxybutyrylamino)ethoxy)ethoxy)acetylamino)ethoxy)ethoxy)acetyl)[Leu¹⁴,²⁸,Lys²⁸]Exendin-4(1-39)amide | RP-HPLC elution at 56.8% acetonitrile<br>Mass confirmed by MALDI |

| Molecule example no. | Data |
|---|---|
| 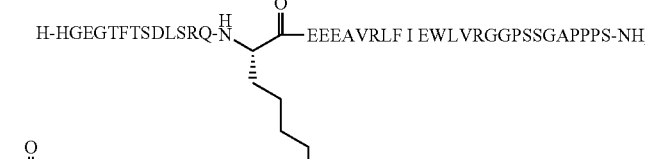

Example 25

N-ε¹⁴-(2-(2-2-(2-(2-(4-(hexadecanoylamino)-4-(S)-carboxybytyrylamino)ethoxy)ethoxy)acetylamino)ethoxy)ethoxy)acetyl[Arg¹²,Lys¹⁴,Val²⁷,Arg²⁸]Exendin-4-(1-39)-amide | HPLC (method B6): RT = 34.37 min Mass confirmed by MALDI 4881 |
| 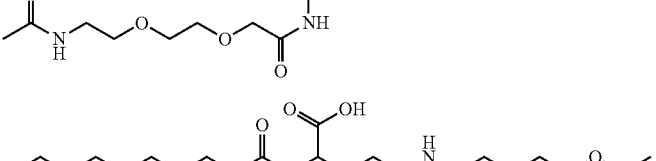

Example 26

N-ε¹⁴-(2-(2-(2-(2-(2-(2-(2-(2-(Octadecanoylamino)ethoxy)ethoxy)acetylamino)ethoxy)ethoxy)acetyl-amino)ethoxy)ethoxy)acetyl)[Arg¹²,Lys¹⁴,Val²⁷,Arg²⁸]Exendin-4-(1-39)-amide | HPLC (method B6): RT = 36.93 min Mass confirmed by MALDI 4926 |
| 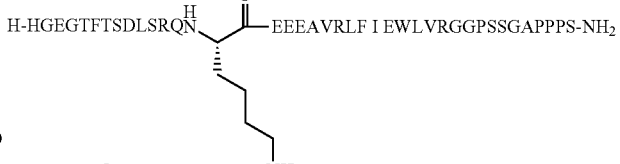

Example 27

N-ε¹⁴-(2-(2-(2-(2-(2-(17-carboxyheptadecanoylamino)ethoxy)ethoxy)acetylamino)ethoxy)ethoxy)acetyl[Arg¹²,Lys¹⁴,Val²⁷,Arg²⁸]Exendin-4-(1-39)-amide | HPLC (method B6): RT = 27.80 Mass confirmed by MALDI 4810 |

| Molecule example no. | Data |
|---|---|
| 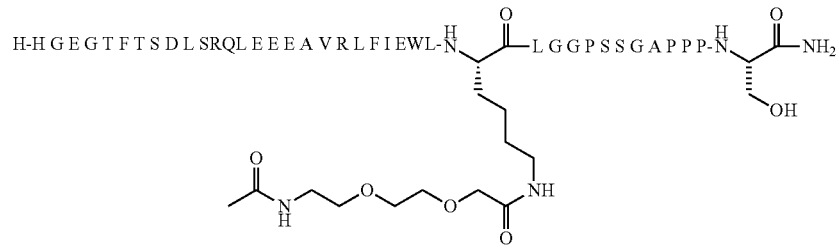<br><br>Example 28<br><br>N-ε²⁷-2-(2-2-(2-(2-(2-(4-(Octadecanoylamino)-4(S)-carboxybutyrylamino)ethoxy)ethoxy)acetylamino)ethoxy)ethoxy)acetyl [Arg¹²,Leu¹⁴,Lys²⁷,Leu²⁸]Exendin-4-(1-39)-amide | HPLC (method B4) RT = 12.97 min LCMS: m/z = 1628.8 (M + 3H)³⁺ Calculated (M + H)⁺ = 4881.6 |
| 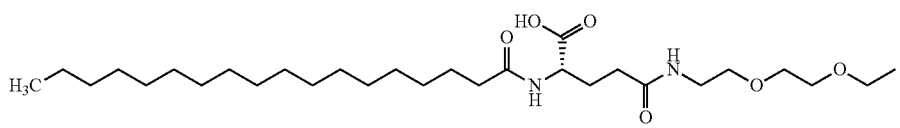<br>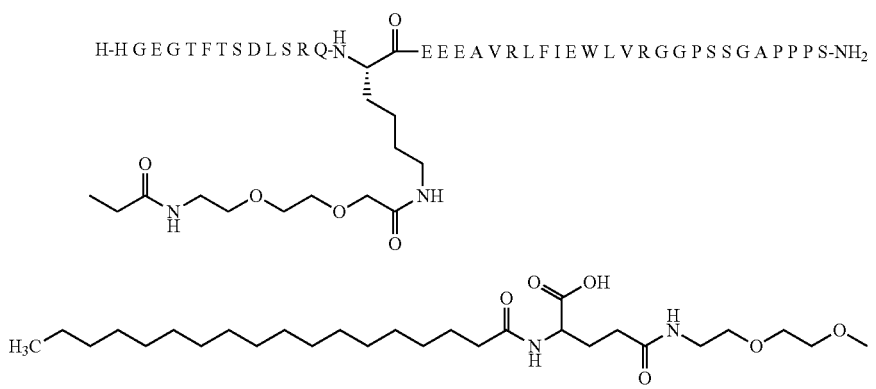<br><br>Example 29<br><br>N-ε¹⁴-(2-(2-(2-(2-(2-(4-(Octadecanoylamino)-4(S)-carboxybutyrylamino)ethoxy)ethoxy)acetylamino)ethoxy)ethoxy)acetyl [Arg¹²,Lys¹⁴,Val²⁷,Arg²⁸]Exendin-4-(1-39)-amide | HPLC (method B6): RT = 30.52 min Mass confirmed by MALDI 4911 |
| 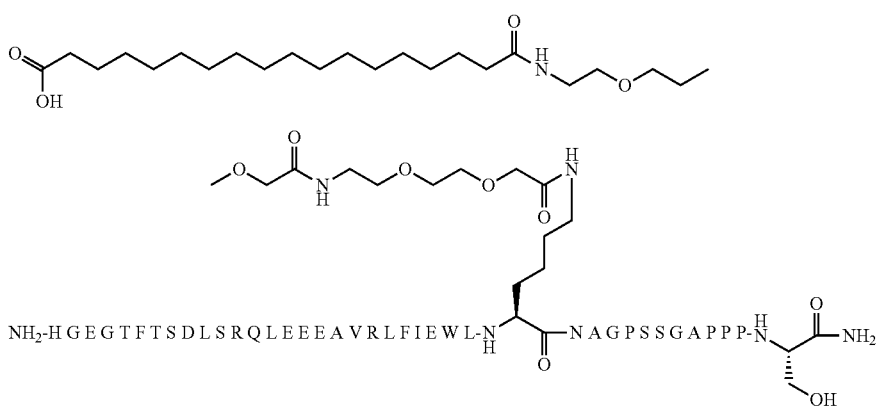<br><br>Example 30<br><br>N-ε²⁷-(2-(2-(2-(2-(2-(17-carboxyheptadecanoylamino)ethoxy)ethoxy)acetylamino)ethoxy)ethoxy)acetyl[Arg¹²,Leu¹⁴,Lys²⁷,Ala²⁹]Exendin-4-(1-39)-amide | HPLC (method B6): RT = 34.24 min LCMS: m/z = 1200.5 (M + 4H)⁴⁺ Calculated (M + H)⁺ = 4797.4 |

-continued

| Molecule example no. | Data |
|---|---|
| 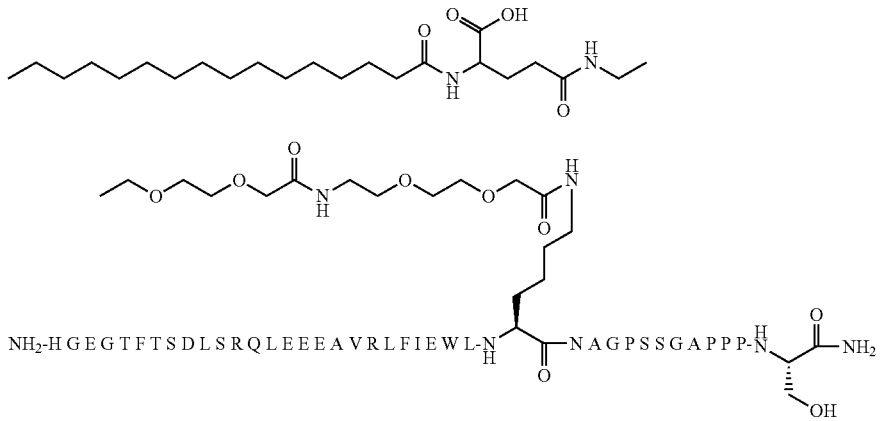

Example 31

N-ε²⁷-[2-(2-[2-(2-[2-(2-[4-hexadecanoylamino-4(S)-carboxybutyrylamino]ethoxy)ethoxy]acetylamino)ethoxy]ethoxy)acetyl][Arg¹²,Leu¹⁴,Lys²⁷,Ala²⁹]Exendin-4-(1-39)-amide | HPLC (method B6): RT = 36.69 min LCMS: m/z = 1218.3 (M + 4H)⁴⁺ Calculated (M + H)⁺ = 4868.5 |
| 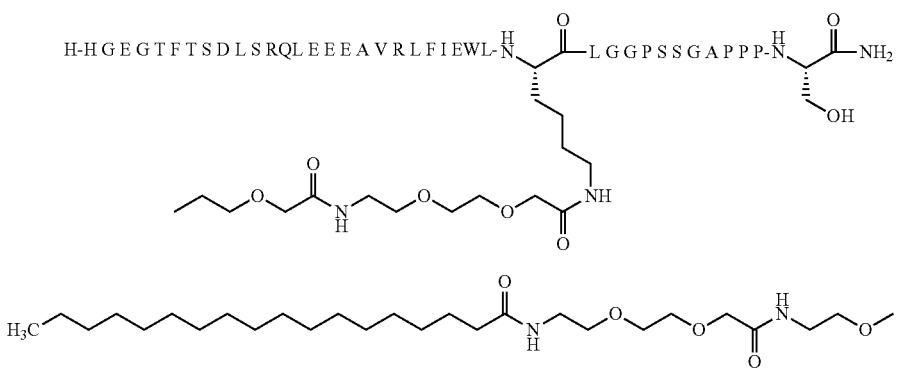

Example 32

N-ε²⁷-2-(2-2-(2-(2-(2-(2-(2-(Octadecanoylamino)ethoxy)ethoxy)acetylamino)ethoxy)ethoxy)acetyl-amino)ethoxy)ethoxy)acetyl[Arg¹²,Leu¹⁴,Lys²⁷,Leu²⁸]Exendin-4-(1-39)-amide | HPLC (method B4): RT = 12.24 min LCMS: m/z = 1633.4 (M + 3H)³⁺ Calculated (M + H)⁺ = 4897.6 |
| 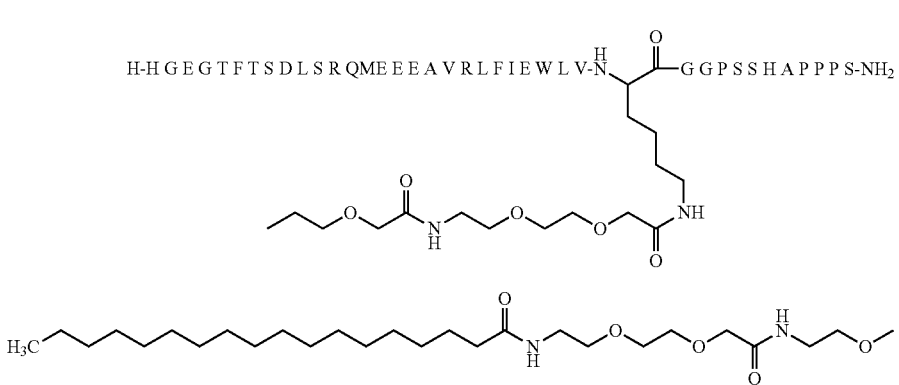

Example 33

N-ε²⁸-(2-(2-(2-(2-(2-(2-(2-(2-(Octadecanoylamino)ethoxy)ethoxy)acetylamino)ethoxy)ethoxy)acetyl-amino)ethoxy)ethoxy)acetyl))[Arg¹²,Val²⁷,Lys²⁸]Exendin-4(1-39)amide | RP-HPLC elution at 56.3% acetonitrile Mass confirmed by MALDI |

| Molecule example no. | Data |
|---|---|
| 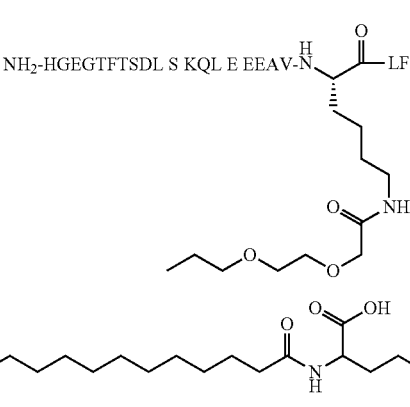 Example 34<br><br>N-ε²⁸-{2-(2-(2-(2-[2-(2-(4-(hexadecanoylamino)-4-carboxybutyrylamino)ethoxy)ethoxy]acetylamino)ethoxy)ethoxy)acetyl)}-[Leu¹⁴,Lys²⁰]Exendin-4-amide | RP-HPLC elution at 49.1% acetonitrile Mass confirmed by MALDI |
| 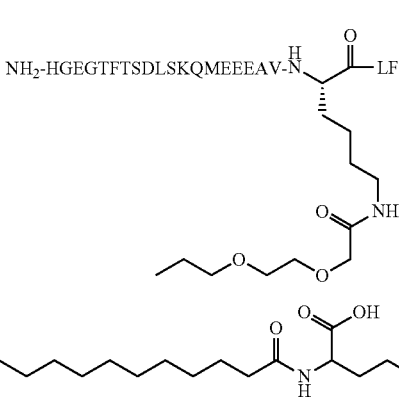 Example 35<br><br>N-ε²⁰-{2-(2-(2-(2-[2-(2-(4-(hexadecanoylamino)-4-carboxybutyrylamino)ethoxy)ethoxy]acetylamino)ethoxy)ethoxy)acetyl)}-[Gln²⁸,Lys²⁰]Exendin-4-amide | RP-HPLC elution at 49.0% acetonitrile Mass confirmed by MALDI |

| Molecule example no. | Data |
|---|---|
| 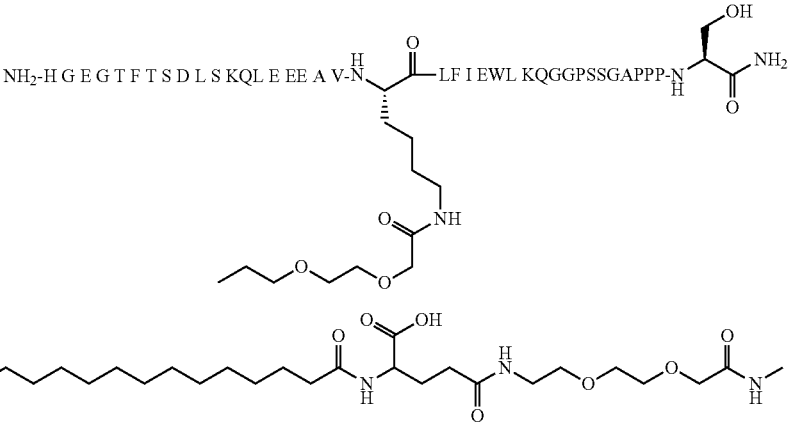<br>Example 36<br>N-ε20-{2-(2-(2-(2-[2-(2-(4-(hexadecanoylamino)-4-carboxybutyrylamino)ethoxy)ethoxy]acetylamino)ethoxy)ethoxy)acetyl)}-[Leu14,Gln28,Lys20]Exendin-4-amide | RP-HPLC elution at 51.0% acetonitrile Mass confirmed by MALDI |
| 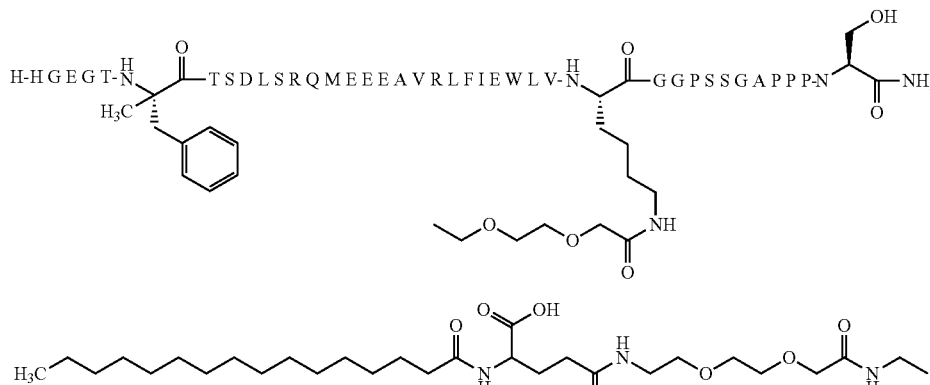<br>Example 37<br>N-ε28-[2-(2-[2-(2-[2-(2-[4-hexadecanoylamino-4(S)-carboxybutyrylamino]ethoxy)ethoxy]acetylamino)ethoxy]ethoxy)acetyl] [alfa-Me-Phe6,Arg12,Val27,Lys28,Ala29]Exendin-4-(1-39)-amide | HPLC (method B6): RT = 37.735 min LCMS: m/z = 1625.0 $(M + 3H)^{3+}$ Calculated $(M + H)^+$ = 4872.6 |

| Molecule example no. | Data |
|---|---|

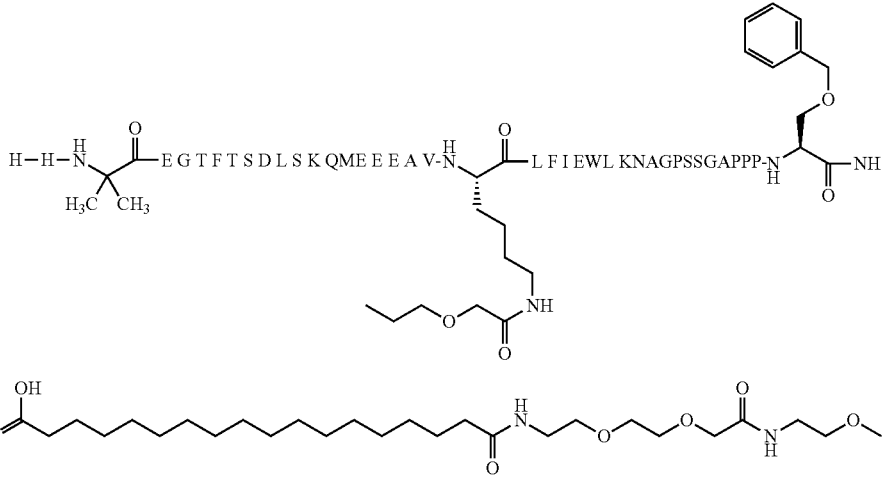

Example 38

N-ε²⁰-(2-(2-(2-(2-(2-(2-(17-carboxyheptadecanoylamino)ethoxy)ethoxy)acetylamino)ethoxy)ethoxy)acetyl[Aib²,Lys²⁰,Ala²⁹,Ser(O-benzyl)³⁹]Exendin-4-(1-39)-amide HPLC (method B6): RT = 34.803 min
LCMS: m/z = 1627.2 (M + 3H)³⁺
Calculated (M + H)⁺ = 4877.6

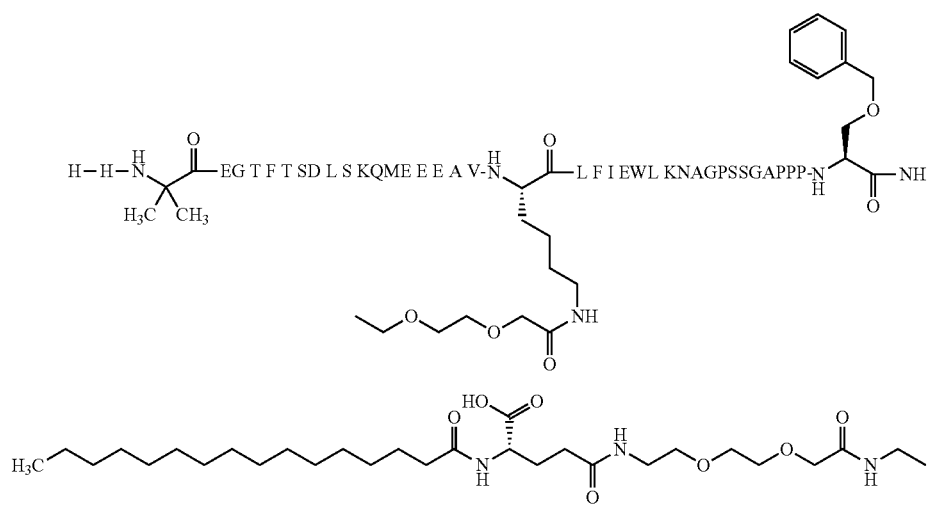

Example 39

N-ε²⁰-[2-(2-[2-(2-[2-(2-[4-(hexadecanoylamino)-4(S)-carboxybutyrylamino]ethoxy)ethoxy]acetylamino)ethoxy]ethoxy)acetyl][Aib²,Lys²⁰,Ala²⁹,Ser(O-benzyl)³⁹]Exendin-4-(1-39)-amide HPLC (method B6): RT = 37.352 min
LCMS: m/z = 1651.1 (M + 3H)³⁺
Calculated (M + H)⁺ = 4948.7

-continued

| Molecule example no. | Data |
|---|---|

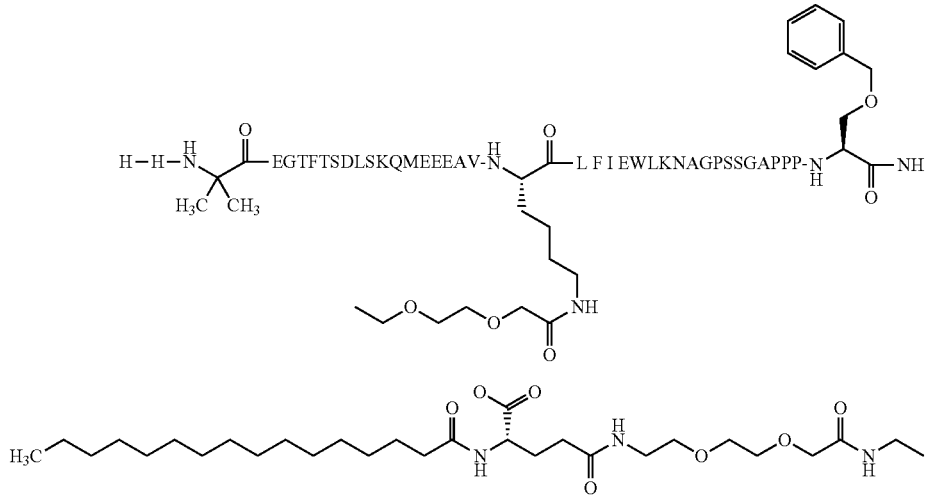

Example 40

N-ε²⁰-[2-(2-[2-(2-[2-(2-[4-(octadecanoylamino)-4(S)-carboxybutyrylamino]ethoxy)ethoxy]acetylamino)ethoxy]ethoxy)acetyl][Aib²,Lys²⁰,Ala²⁹,Ser(O-benzyl)³⁹]Exendin-4-(1-39)-amide HPLC (method B6): RT = 39.166 min
LCMS: m/z = 1659.8 $(M + 3H)^{3+}$
Calculated $(M + H)^+$ = 4976.8

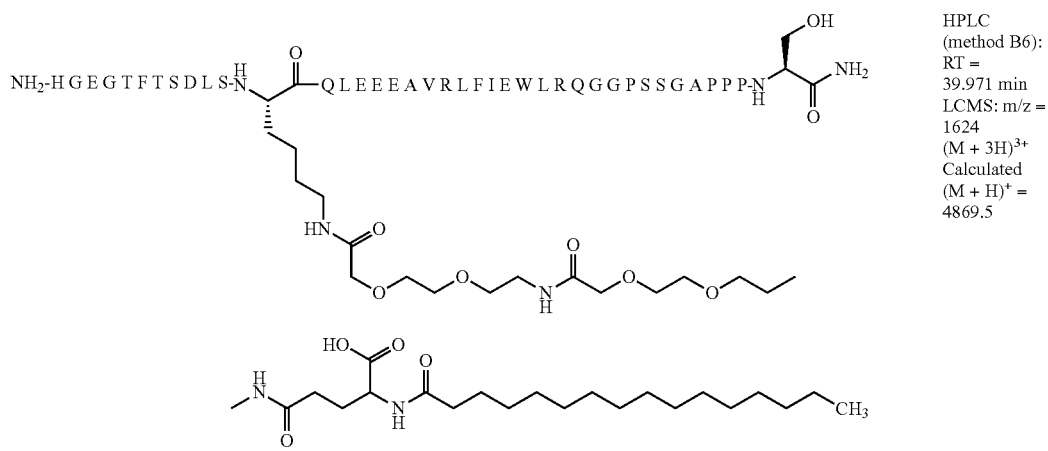

Example 41

N-ε¹²-[2-(2-[2-(2-[2-(2-[4-(hexadecanoylamino)-4(S)-carboxybutyrylamino]ethoxy)ethoxy]acetylamino)ethoxy]ethoxy)acetyl][Lys¹²,Leu¹⁴,Arg²⁷,Gln²⁸]Exendin-4-(1-39)-amide HPLC (method B6): RT = 39.971 min
LCMS: m/z = 1624 $(M + 3H)^{3+}$
Calculated $(M + H)^+$ = 4869.5

| Molecule example no. | Data |
|---|---|
| 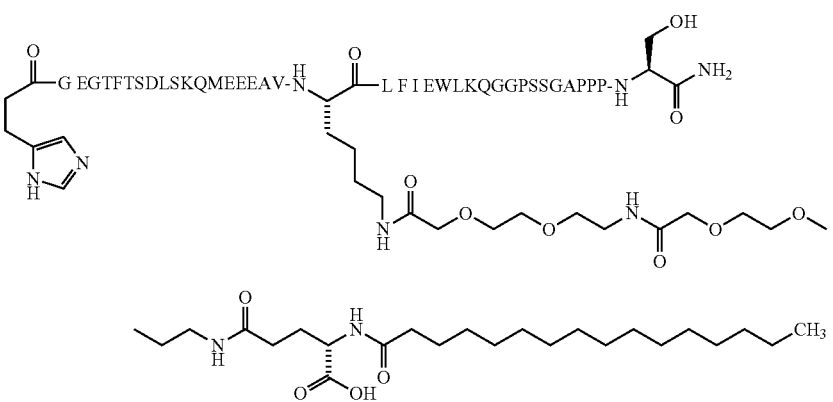<br>Example 42<br>N-ε²⁰-[2-(2-[2-(2-[2-(2-[4-(hexadecanoylamino)-4(S)-carboxybutyrylamino]ethoxy)ethoxy]acetylamino)ethoxy]ethoxy)acetyl][Imidazoylpropionyl¹,Lys²⁰,Gln²⁸]Exendin-4-(1-39)-amide | HPLC (method B6): RT = 35.583 min LCMS: m/z = 1606.1 (M + 3H)³⁺ Calculated (M + H)⁺ = 4815.5 |
| 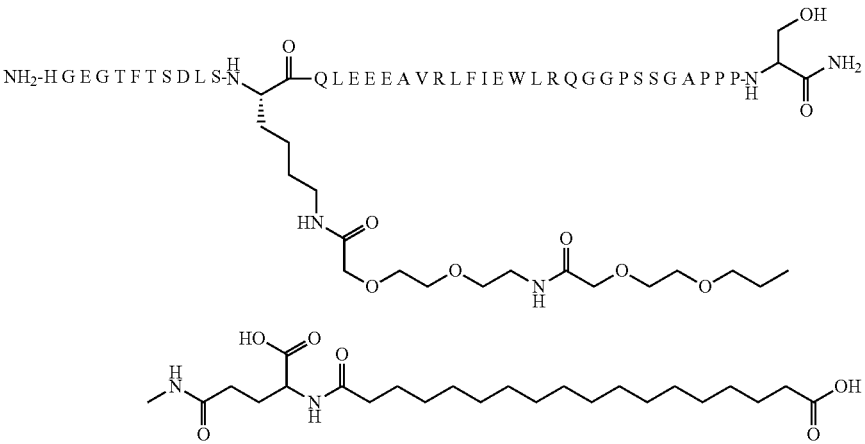<br>Example 43<br>N-ε¹²-[2-(2-[2-(2-[2-(2-[4-(17-carboxyheptadecanoylamino)-4(S)-carboxybutyrylamino]ethoxy)ethoxy]acetylamino)ethoxy]ethoxy)acetyl][Lys¹²,Leu¹⁴,Arg²⁷,Gln²⁸]Exendin-4-(1-39)-amide | HPLC (method B6): RT = 33.821 min LCMS: m/z = 1643 (M + 3H)³⁺ Calculated (M + H)⁺ = 4928.6 |

| Molecule example no. | Data |
|---|---|
| 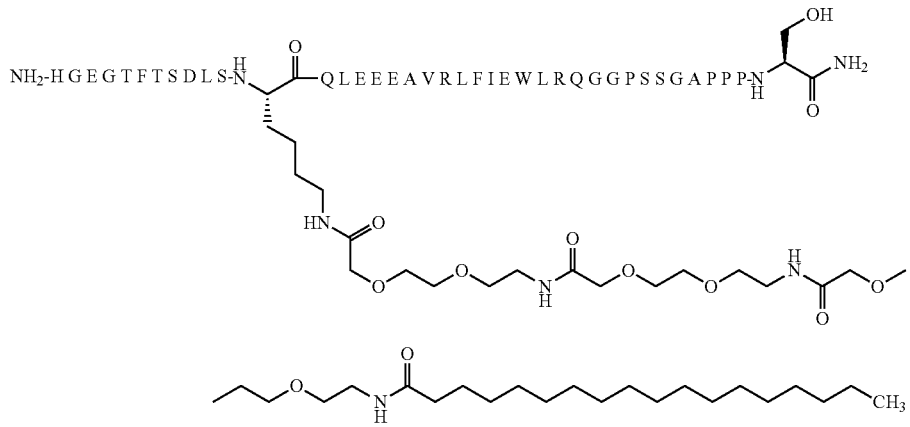<br>Example 44<br>N-ε¹²-(2-(2-(2-(2-(2-(2-(2-(2-Octadecanoylamino)ethoxy)ethoxy)acetylamino)ethoxy)ethoxy)acetylamino)ethoxy)ethoxy)acetyl))[Lys¹²,Leu¹⁴,Arg²⁷,Gln²⁸]Exendin-4-(1-39)-amide | HPLC (method B6): RT = 39.700 min LCMS: m/z = 1638 (M + 3H)³⁺ Calculated (M + H)⁺ = 4913.6 |
| 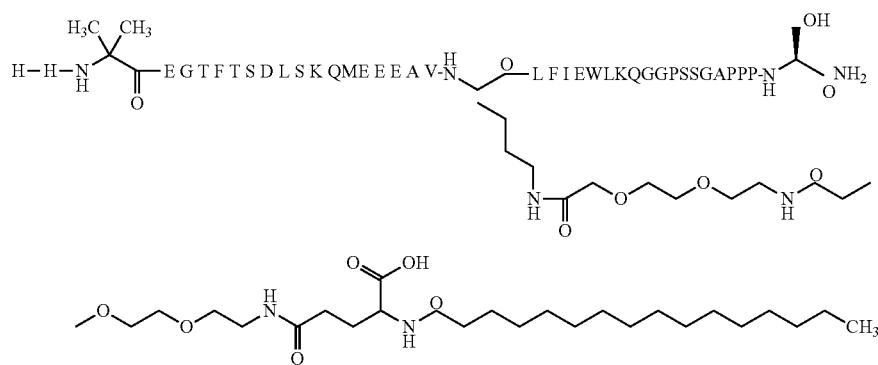<br>Example 45<br>N-epsilon20-{2-(2-(2-(2-[2-(2-(4-(hexadecanoylamino)-4-(S)-carboxybutyrylamino)ethoxy)ethoxy]acetyl)ethoxy)ethoxy)acetyl)}-[[Aib2,Lys20,Gln28]Exendin-4-amide | HPLC (method B6): RT = 35.181 min LCMS: m/z = 1620.3 (M + 3H)³⁺ Calculated (M + H)⁺ = 4858 |
| 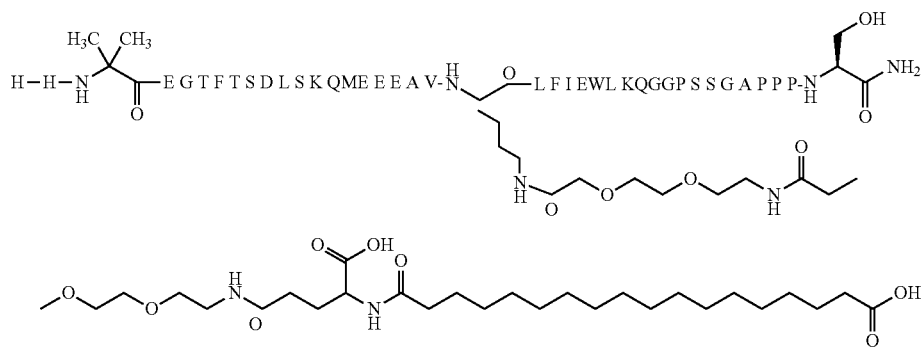<br>Example 46<br>N-ε²⁰-[2-(2-[2-(2-[2-(2-[4-(17-Carboxyheptadecanoylamino)-4(S)-carboxybutyrylamino]ethoxy)ethoxy]acetylamino)ethoxy]ethoxy)acetyl][Aib²;Gln²⁸,Lys²⁰]exendin-4(1-39)amide | HPLC (method B6): RT = 32.212 min LCMS: m/z = 1635.3 (M + 3H)³⁺ Calculated (M + H)⁺ = 4916.6 |

| Molecule example no. | Data |
|---|---|
| 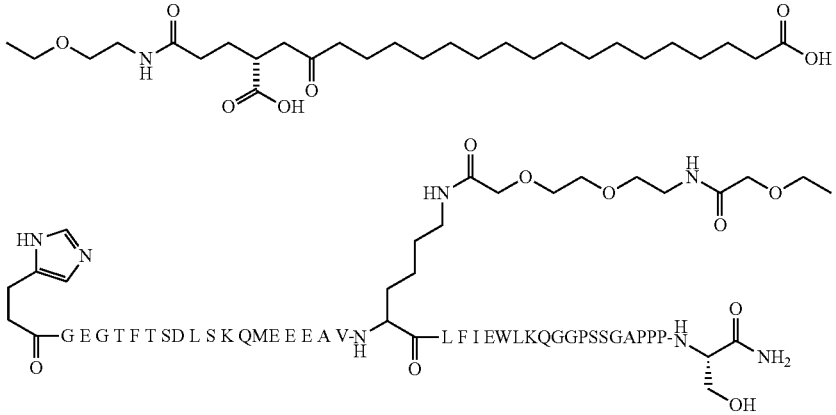<br>Example 47<br><br>N-ε20-[2-(2-[2-(2-[2-(2-[4-(17-Carboxyheptadecanoylamino)-4(S)-carboxybutyrylamino]ethoxy]ethoxy]acetylamino)ethoxy]ethoxy)acetyl] [Imidazoylpropionyl1;Gln28,Lys20]exendin-4(1-39)amide | HPLC (method B6): RT = 32.661 min LCMS: m/z = 1620.8 (M + 3H)3+ Calculated (M + H)+ = 4873.6 |
| 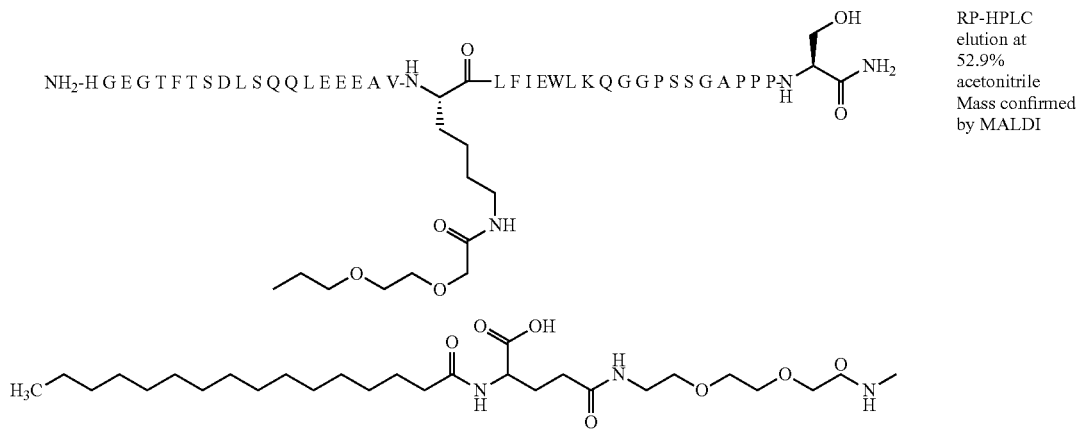<br>Example 48<br><br>N-ε20-{2-(2-(2-(2-[2-(2-(4-(hexadecanoylamino)-4-carboxybutyrylamino)ethoxy)ethoxy]acetylamino)ethoxy)ethoxy)acetyl)}-[Gln12,Leu14,Gln28,Lys20]Exendin-4-amide | RP-HPLC elution at 52.9% acetonitrile Mass confirmed by MALDI |

-continued

| Molecule example no. | Data |
|---|---|
| 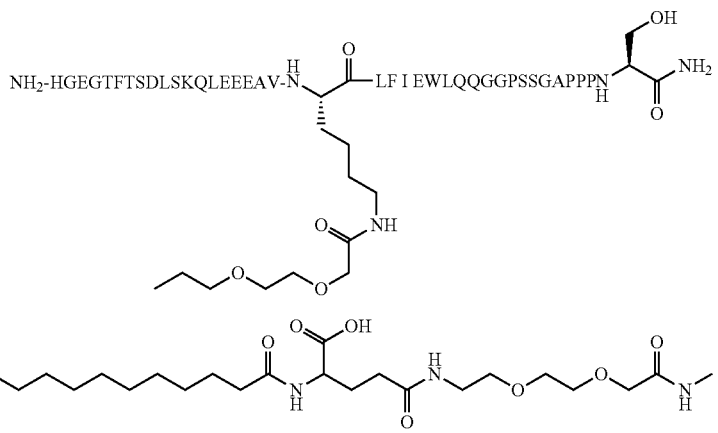 Example 49<br>N-ε[20]-{2-(2-(2-(2-[2-(2-(4-(hexadecanoylamino)-4-carboxybutyrylamino)ethoxy)ethoxy]acetyl)ethoxy)ethoxy)acetyl)}-[Leu[14],Gln[27],Gln[28],Lys[20]]Exendin-4-amide | RP-HPLC elution at 53.0% acetonitrile Mass confirmed by MALDI |
| 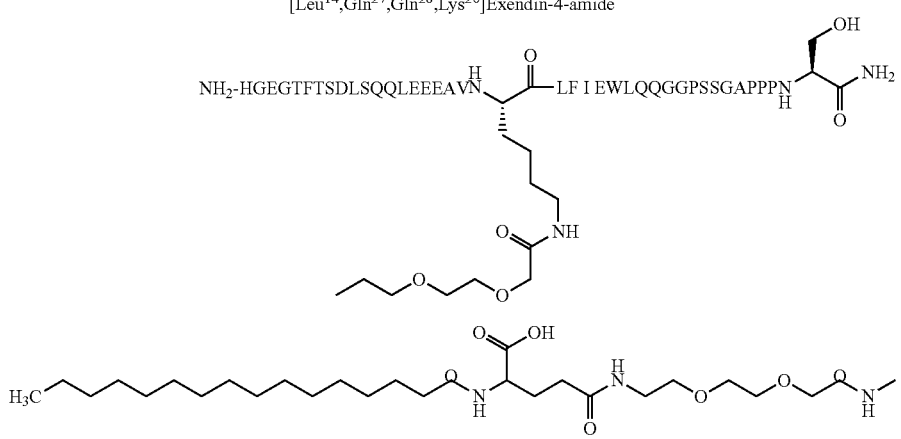 Example 50<br>N-ε[20]-{2-(2-(2-(2-[2-(2-(4-(hexadecanoylamino)-4-carboxybutyrylamino)ethoxy)ethoxy]acetyl)ethoxy)ethoxy)acetyl)}-[Gln[12,27],Leu[14],Lys[20],Gln[28]]Exendin-4-amide | RP-HPLC elution at 56.9% acetonitrile Mass confirmed by MALDI |
| 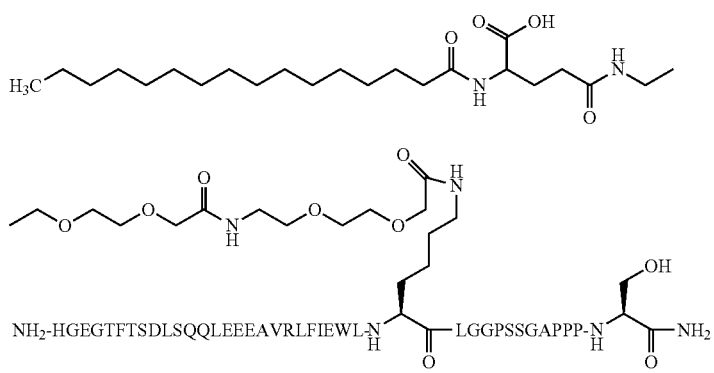 Example 51<br>N-ε[27]-{2-(2-(2-(2-[2-(2-(4-(hexadecanoylamino)-4(S)-carboxybutyrylamino)ethoxy)ethoxy]acetylamino)ethoxy)ethoxy)acetyl)}[Gln[12],Leu[14,28],Lys[27]]Exendin-4(1-39)amide | RP-HPLC elution at 54.7% acetonitrile Mass confirmed by MALDI |

The following compounds may further be prepared according to the procedure above as non-limiting examples of the invention:

| Molecule example no. |
|---|

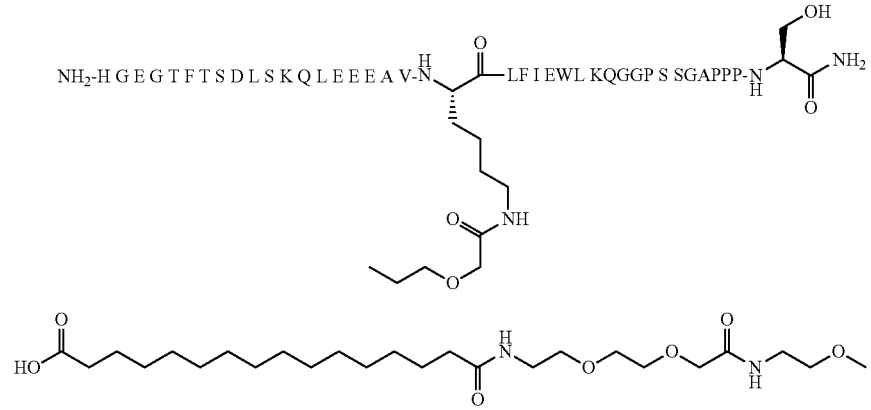

Example 52

N-$\epsilon^{20}$-{2-(2-(2-(2-[2-(2-(15-carboxypentadecanoylamino)ethoxy)ethoxy]acetyl)ethoxy)ethoxy)acetyl)}-[Leu$^{14}$,Gln$^{28}$,Lys$^{20}$] Exendin-4-amide

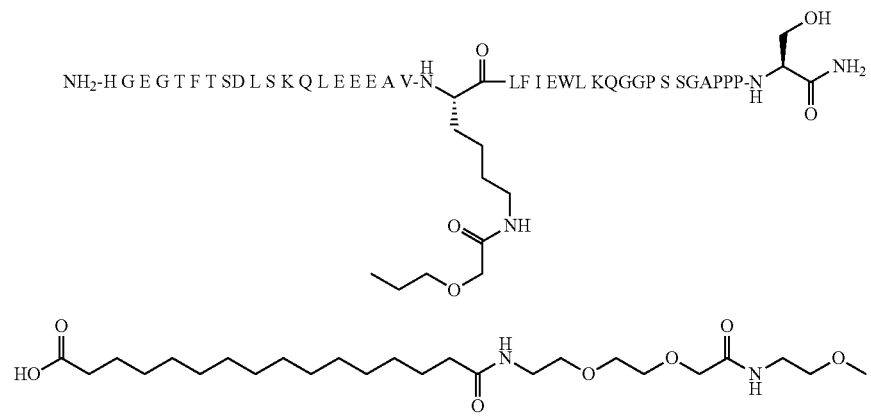

Example 53

N-$\epsilon^{20}$-{2-(2-(2-(2-[2-(2-(13-carboxytridecanoylamino)ethoxy)ethoxy]acetyl)ethoxy)ethoxy)acetyl)}-[Leu$^{14}$,Gln$^{28}$,Lys$^{20}$]Exendin-4-amide

| Molecule example no. |
|---|

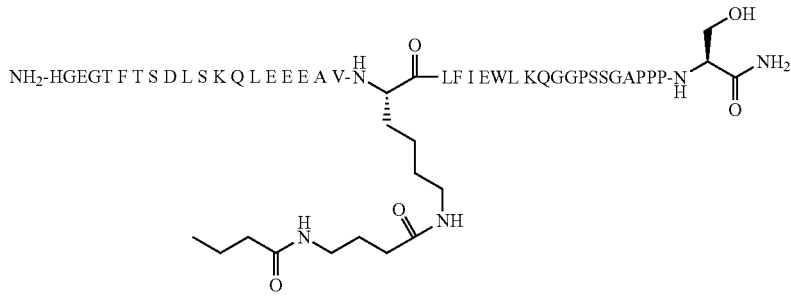

Example 54

N-ε20-(4-(4-(4-(4-(15-carboxypentadecanoylamino)butyrylamino)butyrylamino)butyrylamino)butyrylamino)-[Leu14,Gln28,Lys20]-exendin-4-amide

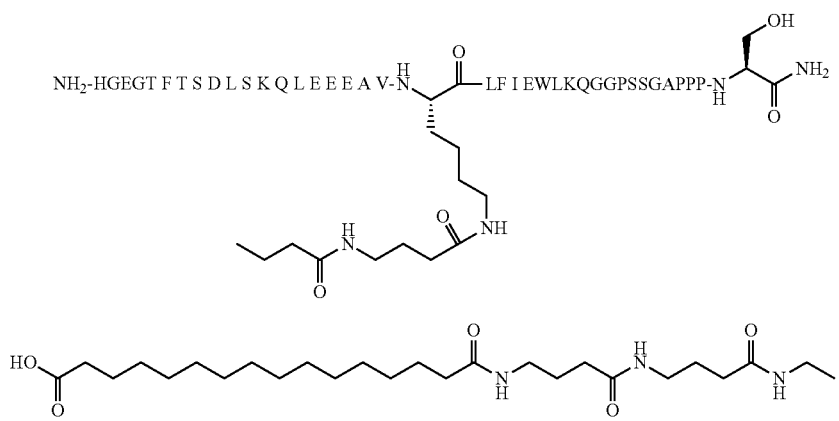

Example 55

N-ε20-(4-(4-(4-(4-(13-carboxytridecanoylamino)butyrylamino)butyrylamino)butyrylamino)butyrylamino)-[Leu14,Gln28, Lys20]-exendin-4-amide

Potency Study

The potency of the compounds of examples 1-51 were determined by calculating the $EC_{50}$ value from the dose-response curve as described on page 11-12 of the description.

The results are shown in the below table:

| Example No. | GLP1cAMPma (3693) [$EC_{50}$ (nM)] Mean Value |
|---|---|
| 1 | 0.007 |
| 2 | 0.027 |
| 3 | 0.025 |
| 4 | 0.027 |
| 5 | 0.007 |
| 6 | 0.018 |
| 7 | 0.012 |
| 8 | 0.44 |
| 9 | 0.61 |
| 10 | 0.35 |
| 11 | 0.52 |
| 12 | 5.45 |
| 13 | 0.27 |
| 14 | 0.017 |
| 15 | 0.044 |
| 16 | 0.093 |
| 17 | 0.025 |
| 18 | 0.033 |
| 19 | 0.24 |
| 20 | 0.08 |
| 21 | 0.19 |
| 22 | 0.017 |
| 23 | 0.71 |
| 24 | 0.022 |
| 25 | 0.037 |
| 26 | 0.088 |
| 27 | 3.65 |
| 28 | 0.14 |
| 29 | 0.059 |
| 30 | 5.6 |

-continued

| Example No. | GLP1cAMPma (3693) [EC$_{50}$ (nM)] Mean Value |
|---|---|
| 31 | 0.15 |
| 32 | 0.049 |
| 33 | 0.041 |
| 34 | 0.011 |
| 35 | 0.033 |
| 36 | 0.023 |
| 37 | 0.052 |
| 38 | 0.23 |
| 39 | 0.008 |
| 40 | 0.006 |
| 41 | 0.006 |
| 42 | 0.042 |
| 43 | 0.22 |
| 44 | 0.0035 |
| 45 | 0.0095 |
| 46 | 0.1 |
| 47 | 2.18 |
| 48 | 0.021 |
| 49 | 0.093 |
| 50 | 0.027 |
| 51 | 0.041 |

Radioligand Binding to Plasma Membranes Expressing the Human GLP-1 Receptor

The binding assay was performed with purified plasma membranes containing the human GLP-1 receptor. The plasma membranes containing the receptors were purified from stably expressing BHK tk-ts 13 cells. The membranes were diluted in Assay Buffer (50 mM HEPES, 5 mM EGTA, 5 mM MgCl$_2$, 0.005% Tween 20, pH=7.4) to a final concentration of 0.2 mg/ml of protein and distributed to 96-well microtiter plates precoated with 0.3% PEI. Membranes in the presence of 0.05 nM [$^{125}$I]GLP-1, unlabelled ligands in increasing concentrations and different HSA concentrations (0.005%, 0.05%, and 2%) were incubated 2 hr at 30° C. After incubation, unbound ligands were separated from bound ligands by filtration through a vacuum-manifold followed by 2×100 μl washing with ice cold assay buffer. The filters were dried overnight at RT, punched out and quantified in a γ-counter.

Pharmacodynamic Study Using Db/Db Mice

The efficacy and duration of action were measured after dosing of 30 nmol/kg to db/db mice. Male db/db mice were shipped from Taconic, Denmark at the age of 8-10 weeks. From the time of arrival, the mice were housed under standard conditions but at 24° C. The mice were kept 10 per cage until experimentation with free access to standard chow (Altromin, Brogaarden APS., Denmark) and tap water at a normal day: light cycle (light on at 6 am). The mice were used for 1 experiment per week for 3 weeks. After this, the mice were euthanized.

After an acclimatisation period of 1 week, the blood glucose was measured by sampling from the tail tip capillary. In brief, 5 μl blood was sampled in heparinised glass capillary tubes and immediately suspended in 250 μl EBIO buffer solution (Eppendorf, Germany) in an 1.5 ml Eppendorf tube. The blood glucose concentration was measured by the glucose oxidase method at the EBIO Plus Auto analyser (Eppendorf, Germany).

The cut of value for blood glucose was 10 mM. When evaluating the mice, it was considered essential, that all 42 mice entering the experiment had blood glucose values above 10 mM, but also that the inter-mice variance was small. Therefore, if many mice were not severely diabetic, whereas some were, the start up of experiments was postponed one week and new basal blood glucose measurements were made.

Based on the basal blood glucose values, the mice were allocated to 7 groups of n=6 with matching group mean blood glucose values.

On the day of testing the basal blood glucose morning values were assessed as described above and the basal body weight of each mouse was assessed. A time 0, the compound was dosed subcutaneously in the scruff of the neck (dosing volume app. 300 μl/50 g mouse).

The blood glucose values were followed up to 48 hours (time 1, 3, 6, 24 and 48 h) and the terminal body weight was assessed.

All data were entered into Graphpad Prism where mean blood glucose and mean delta body weights were calculated.

| Example number | Functional half-life db/db mice hours | ED50 on delta BG in db/db mice pM | Delta AUC for blood glucose after 30 nmol/kg in db/db mice, 48 hours mM × hour |
|---|---|---|---|
| 1 | | | −364 ± 152, *** |
| 3 | | | |
| 5 | | | −410 ± 111, *** |
| 8 | | | −500 ± 122, *** |
| 9 | | | −395 ± 222, *** |
| 10 | | | −410 ± 67, *** |
| 11 | | | −426 ± 151, *** |
| 20 | 5.1 ± 0.9 | 0.73 ± 0.37 | −406 ± 95, *** |
| 21 | | | −426 ± 143, *** |
| 36 | 8.6 ± 1.8 | 0.19 ± 0.09 | |
| 38 | | | −524 ± 179*** |
| 39 | | | −535 ± 172, *** |
| 43 | | | −437 ± 103*** |
| 46 | | | −359 ± 266*** |
| 47 | | | −530 ± 100*** |

One aspect of this invention is to prepare exendin-4 analogues/derivatives with extended plasma half-lives that are suitable for once weekly administration. The pharmacokinetic properties can be evaluated in mini pigs or domestic pigs as described below Pharmacokinetic Screening Pharmacokinetic screening of the peptides of the invention for identification of suitable once weekly candidates were performed on candidates that according to the project screenings plan were shown to be sufficiently potent with respect to glucose lowering potential in a diabetic mouse model (db/db mice) and subsequently had a time of duration of 48 hours or more in the db/db mouse model.

Primary Screening

The first part of the pharmacokinetic screening consisted of a single dose subcutaneous administration of 2 nmol/kg to three minipigs weighing 8-12 kg. Blood samples were drawn from each animal at predose, 0.5, 1, 2, 4, 6, 8, 12, 24, 48, 72, 96 and 120 hours post-injection. All blood samples were stabilised with a special stabilisation buffer consisting of: EDTA (di-sodium) 0.18 M, Aprotenin 15000 KIE/ml, Val-Pyr 0.30 mM, pH adjusted to 7.4 in order to prevent enzymatic degradation of the peptides. Plasma was collected from each stabilised blood samples by centrifugation (4° C., 10 min., 1270 G (4000 rpm), and analysed for the content of the peptide by ELISA assays. Different ELISA assays were used for the plasma analysis. All plasma concentration-time profiles were analysed pharmacokinetically by a non-compartmental analysis. The following pharmacokinetic parameters were calculated if data permitted: $t_{max}$, $C_{max}$, AUC, AUC/Dose, AUC$_{\%Extrapol}$, $\lambda_z$, $t_{1/2}$, CL/F, V$_z$/F and MRT.

Secondary Screening

A second part of the pharmacokinetic screening was conducted on those compounds with an initial terminal half-life of 60-70 hours or more. This screening consisted of a single dose intravenous and subcutaneous administration of 2 nmol/kg to six minipigs for each route of administration. The blood sampling schedule was extended from 0-120 hours to 0-432 and 0-504 hours after intravenous and subcutaneous administration respectively. This was done in order to increase the precision and accuracy of the pharmacokinetic parameter estimates, especially the terminal half-life, AUC and the derived parameters clearance and volume of distribution, and to estimate the bioavailability after subcutaneous administration.

Chemical Stability

The chemical stability of solubilised acylated exendin-4 compounds were monitored by RP-HPLC following incubation at 40° C. for 2.5 weeks of 100 nmol peptide dissolved in 1 ml of phosphate buffered saline containing 150 mM NaCl, 10 mM NaH$_2$PO$_4$, 40 mM Na$_2$HPO$_4$, 0.01% NaN$_3$, pH 7.4.

The formation of exendin analogue related impurities relative to control samples stored in the freezer were monitored with a Waters UPLC system. Samples were applied to Acquity UPLC BEH C18 (1.7 μm) 2.1×50 mm column and eluted at a flow rate of 0.9 ml/min with linear stepwise gradients of acetonitrile in 0.1% trifluoroacetic acid (from 5 to 100% acetonitrile for 10 min, and from 100 to 5% acetonitrile for 1 min). The column was heated to 30 C and detection was performed at 214 nm.

| Example number | Formation rate of peptide related impurities at 40° C. (%/week) |
| --- | --- |
| 14 | 1.5 |
| 20 | 5.0 |
| 21 | 1.5 |
| 22 | 1.5 |
| 24 | 1.0 |
| 25 | 3.0 |
| 26 | 2.0 |
| 29 | 2.0 |
| 36 | 0.5 |
| 40 | 0.5 |

For comparison, the formation rate of peptide related impurities in a 100 nmol/ml solution of Exendin-4 in 50 mM phosphate buffer with 0.05% Tween 80, pH 8.0, was 40-50% per week at 40° C.

The invention claimed is:

1. A compound comprising an amino acid sequence of formula (I):

(SEQ ID No: 1)
$Xaa_1$-$Xaa_2$-Glu-Gly-Thr-$Xaa_6$-Thr-Ser-Asp-Leu-Ser-$Xaa_{12}$-Gln-$Xaa_{14}$-Glu-$Xaa_{16}$-$Xaa_{17}$-Ala-Val-$Xaa_{20}$-$Xaa_{21}$-Phe-Ile-$Xaa_{24}$-Trp-Leu-$Xaa_{27}$-$Xaa_{28}$-$Xaa_{29}$-Gly-Pro-$Xaa_{32}$-Ser-$Xaa_{34}$-Ala-Pro-Pro-Pro-$Xaa_{39}$
Formula (I)

wherein
$Xaa_1$ is L-histidine, imidazoylpropionyl, D-histidine, desamino-histidine, homohistidine, $N^\alpha$-acetyl-histidine, α-methyl-histidine, 3-pyridylalanine, 2-pyridylalanine or 4-pyridylalanine;

$Xaa_2$ is Ala, Gly or Aib;
$Xaa_6$ is Phe or α-methyl-Phe;
$Xaa_{12}$ is Lys, Arg or Gln;
$Xaa_{14}$ is Lys;
$Xaa_{16}$ is Gly, Glu or Aib;
$Xaa_{17}$ is Gln or Glu;
$Xaa_{20}$ is Lys, Glu or Arg;
$Xaa_{21}$ is Glu or Leu;
$Xaa_{24}$ is Ala, Glu or Arg;
$Xaa_{27}$ is Val, Lys, Gln or Arg;
$Xaa_{28}$ is Lys, Leu, Glu, Asn, Gln or Arg;
$Xaa_{29}$ is Gly, Ala or Aib;
$Xaa_{32}$ is Ser or Lys;
$Xaa_{34}$ is Gly or Lys;
$Xaa_{39}$ is Ser or O-Benzyl-Ser;

the C-terminus may optionally be derivatized as an amide;
and wherein Lys14 in formula I is derivatized with A-(B)$_r$—(C)$_s$— to give an acylated Lys residue, wherein C, which is independently selected s times, where s is 0, 1, 2, 3 or 4, is represented by:

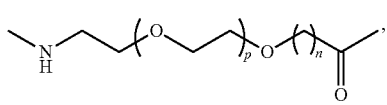

wherein p is 1, 2, 3, 4, 5, 6, 7, 8, 9, 10, 11, 12, 13, 14, 15, 16, 17, 18, 19, 20, 21, 22, or 23
and n is 1, 2, 3 or 4;
and wherein B is

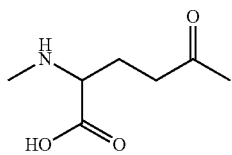

selected r times, where r is 0, 1, 2 or 3,
and
wherein A is a group selected from

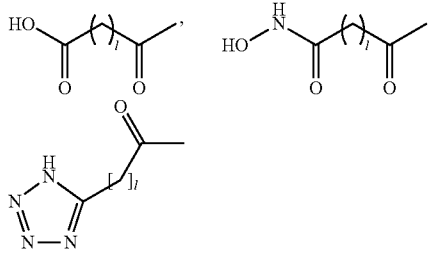

and CH$_3$(CH$_2$)$_l$—C(=O)—
where l is 12, 13, 14, 15, 16, 17, 18, 19 or 20;
with the proviso that at least two amino acids selected from Xaa$_1$, Xaa$_2$, Xaa$_6$, Xaa$_{12}$, Xaa$_{16}$, Xaa$_{17}$, Xaa$_{20}$, Xaa$_{21}$, Xaa$_{24}$, Xaa$_{27}$, Xaa$_{28}$, Xaa$_{29}$, Xaa$_{32}$, Xaa$_{34}$ and Xaa$_{39}$
are different from the corresponding amino acids in exendin-4.

2. A compound according to claim 1 wherein
Xaa$_1$ is L-histidine, imidazoylpropionyl or des-amino Histidine;
Xaa$_2$ is Gly or Aib;
Xaa$_6$ is Phe or α-methyl-Phe;
Xaa$_{12}$ is Lys, Arg or Gln;
Xaa$_{14}$ is Lys;
Xaa$_{16}$ is Glu;
Xaa$_{17}$ is Glu;
Xaa$_{20}$ is Lys;
Xaa$_{21}$ is Leu;
Xaa$_{24}$ is Glu;
Xaa$_{27}$ is Val, Lys, Gln or Arg;
Xaa$_{28}$ is Lys, Leu, Glu, Asn, Gln or Arg;
Xaa$_{29}$ is Gly or Ala;
Xaa$_{32}$ is Ser or Lys;
Xaa$_{34}$ is Gly or Lys;
Xaa$_{39}$ is Ser or O-Benzyl-Ser;
the C-terminus may optionally be derivatized as an amide;
and wherein Lys14 in formula I is derivatized with A-(B)$_r$—(C)$_s$— to give an acylated Lys residue, wherein C, which is independently selected s times, wherein s is 0, 1, 2, 3 or 4, is represented by:

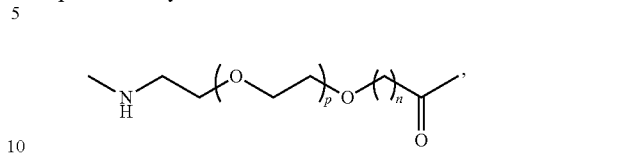

wherein p is 1, 2, 3, 4, 5, 6, 7, 8, 9, 10, 11, 12, 13, 14, 15, 16, 17, 18, 19, 20, 21, 22, or 23
and n is 1, 2 or 3;
and wherein B is

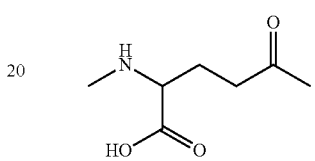

selected r times, where r is 0, 1, 2 or 3,
and
wherein A is a group selected from

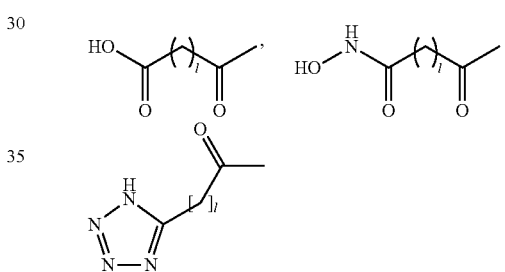

and CH$_3$(CH$_2$)$_l$—C(=O)—
where l is 12, 13, 14, 15, 16, 17, 18, 19 or 20;
with the proviso that at least two amino acids selected from Xaa$_1$, Xaa$_2$, Xaa$_6$, Xaa$_{12}$, Xaa$_{20}$, Xaa$_{24}$, Xaa$_{27}$, Xaa$_{28}$, Xaa$_{29}$, Xaa$_{32}$, Xaa$_{34}$ and Xaa$_{39}$
are different from the corresponding amino acids in exendin-4.

3. A compound according to claim 2, wherein Xaa$_{12}$ is Arg.
4. A compound according to claim 3, wherein Xaa$_1$ is L-histidine or des-amino histidine.
5. A compound according to claim 4, wherein Xaa$_{27}$ is Val.
6. A compound according to claim 5, wherein Xaa$_{28}$ is Arg.
7. A compound according to claim 1, wherein r is 1.
8. A compound according to claim 1, wherein s is 2.
9. A compound according to claim 1, wherein p is 1.
10. A compound according to claim 1, wherein A is

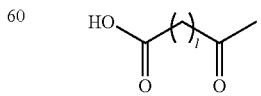

or CH$_3$(CH$_2$)$_l$—C(=O)—.
11. A compound according to claim 1, wherein l is 13, 14, 15, 16, 17 or 18.

12. A pharmaceutical composition comprising a compound according to claim 1, and a pharmaceutically acceptable excipient.

13. A method for treating a subject suffering from hyperglycemia, type 2 diabetes, impaired glucose tolerance, type 1 diabetes, obesity, hypertension, syndrome X, dyslipidemia, cognitive disorders, atherosclerosis, myocardial infarction, coronary heart disease, Alzheimer's disease, stroke, inflammatory bowel syndrome, dyspepsia or gastric ulcers, said method comprising administering to said subject a therapeutically effective amount of the pharmaceutical composition of claim 12.

14. A method for delaying disease progression in type 2 diabetes in a subject, said method comprising administering to said subject a therapeutically effective amount of the pharmaceutical composition of claim 12.

15. A compound according to claim 1 which is selected from the following compounds:

N-$\epsilon^{14}$-(2-(2-(2-(2-(2-(4-(hexadecanoylamino)-4-(S)-carboxybutyrylamino)ethoxy)ethoxy)acetylamino)ethoxy)ethoxy)acetyl[Arg$^{12}$,Lys$^{14}$,Val$^{27}$,Arg$^{28}$]Exendin-4-(1-39)-amide, N-$\epsilon^{14}$-(2-(2-(2-(2-(2-(2-(2-(2-(2-(Octadecanoylamino)ethoxy)ethoxy)acetylamino)ethoxy)ethoxy)acetylamino)ethoxy)ethoxy)acetyl)[Arg$^{12}$,Lys$^{14}$,Val$^{27}$,Arg$^{28}$]Exendin-4-(1-39)-amide, and N-$\epsilon^{14}$-(2-(2-(2-(2-(2-(2-(17-carboxyheptadecanoylamino)ethoxy)ethoxy)acetylamino)ethoxy)ethoxy)acetyl[Arg$^{12}$,Lys$^{14}$,Val$^{27}$,Arg$^{28}$]Exendin-4-(1-39)-amide.

16. A pharmaceutical composition comprising a compound according to claim 15, and a pharmaceutically acceptable excipient.

17. A method for treating a subject suffering from hyperglycemia, type 2 diabetes, impaired glucose tolerance, type 1 diabetes, obesity, hypertension, syndrome X, dyslipidemia, cognitive disorders, atherosclerosis, myocardial infarction, coronary heart disease, Alzheimer's disease, stroke, inflammatory bowel syndrome, dyspepsia or gastric ulcers, said method comprising administering to said subject a therapeutically effective amount of the pharmaceutical composition of claim 16.

18. A method for delaying disease progression in type 2 diabetes in a subject, said method comprising administering to said subject a therapeutically effective amount of the pharmaceutical composition of claim 16.

* * * * *

SEQUENCE LISTING

<160> NUMBER OF SEQ ID NOS: 26

<210> SEQ ID NO 1
<211> LENGTH: 39
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is L-histidine, imidazoylpropionyl,
      D-histidine, desamino-histidine, 2-amino-histidine, homohistidine,
      Nalpha-acetyl-histidine, alpha-methyl-histidine,
      3-pyridylalanine, 2-pyridylalanine or 4-pyridylalanine
<220> FEATURE:
<221> NAME/KEY: MISC_FEATURE
<222> LOCATION: (2)..(2)
<223> OTHER INFORMATION: Xaa is Ala, Gly or Aib
<220> FEATURE:
<221> NAME/KEY: MISC_FEATURE
<222> LOCATION: (6)..(6)
<223> OTHER INFORMATION: Xaa is Phe or alpha-methyl-Phe
<220> FEATURE:
<221> NAME/KEY: MISC_FEATURE
<222> LOCATION: (12)..(12)
<223> OTHER INFORMATION: Xaa is Lys, Arg or Gln
<220> FEATURE:
<221> NAME/KEY: MISC_FEATURE
<222> LOCATION: (14)..(14)
<223> OTHER INFORMATION: Xaa is Leu, Lys, Met, Ile or Nle
<220> FEATURE:
<221> NAME/KEY: MISC_FEATURE
<222> LOCATION: (16)..(16)
<223> OTHER INFORMATION: Xaa is Gly, Glu or Aib
<220> FEATURE:
<221> NAME/KEY: MISC_FEATURE
<222> LOCATION: (17)..(17)
<223> OTHER INFORMATION: Xaa is Gln or Glu
<220> FEATURE:
<221> NAME/KEY: MISC_FEATURE
<222> LOCATION: (20)..(20)
<223> OTHER INFORMATION: Xaa is Lys, Glu or Arg
<220> FEATURE:
<221> NAME/KEY: MISC_FEATURE
<222> LOCATION: (21)..(21)
<223> OTHER INFORMATION: Xaa is Glu or Leu
<220> FEATURE:

```
<221> NAME/KEY: MISC_FEATURE
<222> LOCATION: (24)..(24)
<223> OTHER INFORMATION: Xaa is Ala, Glu or Arg
<220> FEATURE:
<221> NAME/KEY: MISC_FEATURE
<222> LOCATION: (27)..(27)
<223> OTHER INFORMATION: Xaa is Val, Lys, Gln or Arg
<220> FEATURE:
<221> NAME/KEY: MISC_FEATURE
<222> LOCATION: (28)..(28)
<223> OTHER INFORMATION: Xaa is Lys, Leu, Glu, Asn, Gln or Arg
<220> FEATURE:
<221> NAME/KEY: MISC_FEATURE
<222> LOCATION: (29)..(29)
<223> OTHER INFORMATION: Xaa is Gly, Ala or Aib
<220> FEATURE:
<221> NAME/KEY: MISC_FEATURE
<222> LOCATION: (32)..(32)
<223> OTHER INFORMATION: Xaa is Ser or Lys
<220> FEATURE:
<221> NAME/KEY: MISC_FEATURE
<222> LOCATION: (34)..(34)
<223> OTHER INFORMATION: Xaa is Gly or Lys
<220> FEATURE:
<221> NAME/KEY: MISC_FEATURE
<222> LOCATION: (39)..(39)
<223> OTHER INFORMATION: Xaa is Ser or O-Benzyl-Ser

<400> SEQUENCE: 1

Xaa Xaa Glu Gly Thr Xaa Thr Ser Asp Leu Ser Xaa Gln Xaa Glu Xaa
1               5                   10                  15

Xaa Ala Val Xaa Xaa Phe Ile Xaa Trp Leu Xaa Xaa Xaa Gly Pro Xaa
            20                  25                  30

Ser Xaa Ala Pro Pro Pro Xaa
        35

<210> SEQ ID NO 2
<211> LENGTH: 39
<212> TYPE: PRT
<213> ORGANISM: Artificial Sequence
<220> FEATURE:
<223> OTHER INFORMATION: SYNTHETIC

<400> SEQUENCE: 2

His Gly Glu Gly Thr Phe Thr Ser Asp Leu Ser Arg Gln Leu Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 3
<211> LENGTH: 39
<212> TYPE: PRT
<213> ORGANISM: Artificial Sequence
<220> FEATURE:
<223> OTHER INFORMATION: SYNTHETIC

<400> SEQUENCE: 3

His Gly Glu Gly Thr Phe Thr Ser Asp Leu Ser Arg Gln Leu Glu Glu
1               5                   10                  15

Glu Ala Val Arg Leu Phe Ile Glu Trp Leu Val Arg Gly Gly Pro Lys
            20                  25                  30

Ser Gly Ala Pro Pro Pro Ser
        35

<210> SEQ ID NO 4
```

```
<211> LENGTH: 39
<212> TYPE: PRT
<213> ORGANISM: Artificial Sequence
<220> FEATURE:
<223> OTHER INFORMATION: SYNTHETIC

<400> SEQUENCE: 4

His Gly Glu Gly Thr Phe Thr Ser Asp Leu Ser Arg Gln Leu Glu Glu
1               5                   10                  15

Glu Ala Val Arg Leu Phe Ile Glu Trp Leu Val Lys Gly Gly Pro Ser
            20                  25                  30

Ser Gly Ala Pro Pro Pro Ser
        35

<210> SEQ ID NO 5
<211> LENGTH: 39
<212> TYPE: PRT
<213> ORGANISM: Artificial Sequence
<220> FEATURE:
<223> OTHER INFORMATION: SYNTHETIC

<400> SEQUENCE: 5

His Gly Glu Gly Thr Phe Thr Ser Asp Leu Ser Arg Gln Leu Glu Glu
1               5                   10                  15

Glu Ala Val Lys Leu Phe Ile Glu Trp Leu Arg Arg Gly Gly Pro Ser
            20                  25                  30

Ser Gly Ala Pro Pro Pro Ser
        35

<210> SEQ ID NO 6
<211> LENGTH: 39
<212> TYPE: PRT
<213> ORGANISM: Artificial Sequence
<220> FEATURE:
<223> OTHER INFORMATION: SYNTHETIC

<400> SEQUENCE: 6

His Gly Glu Gly Thr Phe Thr Ser Asp Leu Ser Arg Gln Leu Glu Glu
1               5                   10                  15

Glu Ala Val Arg Leu Phe Ile Glu Trp Leu Arg Asn Gly Gly Pro Ser
            20                  25                  30

Ser Lys Ala Pro Pro Pro Ser
        35

<210> SEQ ID NO 7
<211> LENGTH: 39
<212> TYPE: PRT
<213> ORGANISM: Artificial Sequence
<220> FEATURE:
<223> OTHER INFORMATION: SYNTHETIC

<400> SEQUENCE: 7

His Gly Glu Gly Thr Phe Thr Ser Asp Leu Ser Arg Gln Leu Glu Glu
1               5                   10                  15

Glu Ala Val Lys Leu Phe Ile Glu Trp Leu Arg Gln Gly Gly Pro Ser
            20                  25                  30

Ser Gly Ala Pro Pro Pro Ser
        35

<210> SEQ ID NO 8
<211> LENGTH: 39
<212> TYPE: PRT
<213> ORGANISM: Artificial Sequence
```

<220> FEATURE:
<223> OTHER INFORMATION: SYNTHETIC

<400> SEQUENCE: 8

His Gly Glu Gly Thr Phe Thr Ser Asp Leu Ser Arg Gln Leu Glu Glu
1               5                   10                  15
Glu Ala Val Arg Leu Phe Ile Glu Trp Leu Val Arg Gly Gly Pro Lys
            20                  25                  30
Ser Gly Ala Pro Pro Ser
        35

<210> SEQ ID NO 9
<211> LENGTH: 39
<212> TYPE: PRT
<213> ORGANISM: Artificial Sequence
<220> FEATURE:
<223> OTHER INFORMATION: SYNTHETIC

<400> SEQUENCE: 9

His Gly Glu Gly Thr Phe Thr Ser Asp Leu Ser Arg Gln Leu Glu Glu
1               5                   10                  15
Glu Ala Val Arg Leu Phe Ile Glu Trp Leu Lys Leu Gly Gly Pro Ser
            20                  25                  30
Ser Gly Ala Pro Pro Ser
        35

<210> SEQ ID NO 10
<211> LENGTH: 39
<212> TYPE: PRT
<213> ORGANISM: Artificial Sequence
<220> FEATURE:
<223> OTHER INFORMATION: SYNTHETIC

<400> SEQUENCE: 10

His Gly Glu Gly Thr Phe Thr Ser Asp Leu Ser Arg Gln Leu Glu Glu
1               5                   10                  15
Glu Ala Val Arg Leu Phe Ile Glu Trp Leu Lys Asn Ala Gly Pro Ser
            20                  25                  30
Ser Gly Ala Pro Pro Ser
        35

<210> SEQ ID NO 11
<211> LENGTH: 39
<212> TYPE: PRT
<213> ORGANISM: Artificial Sequence
<220> FEATURE:
<223> OTHER INFORMATION: SYNTHETIC

<400> SEQUENCE: 11

His Gly Glu Gly Thr Phe Thr Ser Asp Leu Ser Lys Gln Leu Glu Glu
1               5                   10                  15
Glu Ala Val Arg Leu Phe Ile Glu Trp Leu Lys Leu Gly Gly Pro Ser
            20                  25                  30
Ser Gly Ala Pro Pro Ser
        35

<210> SEQ ID NO 12
<211> LENGTH: 39
<212> TYPE: PRT
<213> ORGANISM: Artificial Sequence
<220> FEATURE:
<223> OTHER INFORMATION: SYNTHETIC

```
<400> SEQUENCE: 12

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Leu Gly Gly Pro Ser
            20                  25                  30

Ser Gly Ala Pro Pro Ser
        35

<210> SEQ ID NO 13
<211> LENGTH: 39
<212> TYPE: PRT
<213> ORGANISM: Artificial Sequence
<220> FEATURE:
<223> OTHER INFORMATION: SYNTHETIC

<400> SEQUENCE: 13

His Gly Glu Gly Thr Phe Thr Ser Asp Leu Ser Arg Gln Lys Glu Glu
1               5                   10                  15

Glu Ala Val Arg Leu Phe Ile Glu Trp Leu Val Arg Gly Gly Pro Ser
            20                  25                  30

Ser Gly Ala Pro Pro Ser
        35

<210> SEQ ID NO 14
<211> LENGTH: 39
<212> TYPE: PRT
<213> ORGANISM: Artificial Sequence
<220> FEATURE:
<223> OTHER INFORMATION: SYNTHETIC

<400> SEQUENCE: 14

His Gly Glu Gly Thr Phe Thr Ser Asp Leu Ser Arg Gln Met Glu Glu
1               5                   10                  15

Glu Ala Val Arg Leu Phe Ile Glu Trp Leu Val Lys Gly Gly Pro Ser
            20                  25                  30

Ser Gly Ala Pro Pro Ser
        35

<210> SEQ ID NO 15
<211> LENGTH: 39
<212> TYPE: PRT
<213> ORGANISM: Artificial Sequence
<220> FEATURE:
<223> OTHER INFORMATION: SYNTHETIC

<400> SEQUENCE: 15

His Gly Glu Gly Thr Phe Thr Ser Asp Leu Ser Lys Gln Leu Glu Glu
1               5                   10                  15

Glu Ala Val Lys Leu Phe Ile Glu Trp Leu Lys Asn Gly Gly Pro Ser
            20                  25                  30

Ser Gly Ala Pro Pro Ser
        35

<210> SEQ ID NO 16
<211> LENGTH: 39
<212> TYPE: PRT
<213> ORGANISM: Artificial Sequence
<220> FEATURE:
<223> OTHER INFORMATION: SYNTHETIC

<400> SEQUENCE: 16

His Gly Glu Gly Thr Phe Thr Ser Asp Leu Ser Lys Gln Met Glu Glu
```

```
                  1               5                  10                 15
              Glu Ala Val Lys Leu Phe Ile Glu Trp Leu Lys Gln Gly Gly Pro Ser
                          20                  25                  30

Ser Gly Ala Pro Pro Ser
                      35

<210> SEQ ID NO 17
<211> LENGTH: 39
<212> TYPE: PRT
<213> ORGANISM: Artificial Sequence
<220> FEATURE:
<223> OTHER INFORMATION: SYNTHETIC

<400> SEQUENCE: 17

His Gly Glu Gly Thr Phe Thr Ser Asp Leu Ser Lys Gln Leu Glu Glu
1               5                  10                  15

Glu Ala Val Lys Leu Phe Ile Glu Trp Leu Lys Gln Gly Gly Pro Ser
            20                  25                  30

Ser Gly Ala Pro Pro Ser
        35

<210> SEQ ID NO 18
<211> LENGTH: 39
<212> TYPE: PRT
<213> ORGANISM: Artificial Sequence
<220> FEATURE:
<223> OTHER INFORMATION: SYNTHETIC
<220> FEATURE:
<221> NAME/KEY: MISC_FEATURE
<222> LOCATION: (6)..(6)
<223> OTHER INFORMATION: X = alpha-Me-Phe

<400> SEQUENCE: 18

His Gly Glu Gly Thr Xaa Thr Ser Asp Leu Ser Arg Gln Met Glu Glu
1               5                  10                  15

Glu Ala Val Arg Leu Phe Ile Glu Trp Leu Val Lys Gly Gly Pro Ser
            20                  25                  30

Ser Gly Ala Pro Pro Ser
        35

<210> SEQ ID NO 19
<211> LENGTH: 39
<212> TYPE: PRT
<213> ORGANISM: Artificial Sequence
<220> FEATURE:
<223> OTHER INFORMATION: SYNTHETIC
<220> FEATURE:
<221> NAME/KEY: MISC_FEATURE
<222> LOCATION: (2)..(2)
<223> OTHER INFORMATION: x = Aib
<220> FEATURE:
<221> NAME/KEY: MISC_FEATURE
<222> LOCATION: (39)..(39)
<223> OTHER INFORMATION: x = Ser(O-benzyl)

<400> SEQUENCE: 19

His Xaa Glu Gly Thr Phe Thr Ser Asp Leu Ser Lys Gln Met Glu Glu
1               5                  10                  15

Glu Ala Val Lys Leu Phe Ile Glu Trp Leu Lys Asn Ala Gly Pro Ser
            20                  25                  30

Ser Gly Ala Pro Pro Xaa
        35

<210> SEQ ID NO 20
```

```
<211> LENGTH: 39
<212> TYPE: PRT
<213> ORGANISM: Artificial Sequence
<220> FEATURE:
<223> OTHER INFORMATION: SYNTHETIC

<400> SEQUENCE: 20

His Gly Glu Gly Thr Phe Thr Ser Asp Leu Ser Lys Gln Leu Glu
1               5                   10                  15

Glu Ala Val Arg Leu Phe Ile Glu Trp Leu Arg Gln Gly Gly Pro Ser
                20                  25                  30

Ser Gly Ala Pro Pro Pro Ser
            35

<210> SEQ ID NO 21
<211> LENGTH: 39
<212> TYPE: PRT
<213> ORGANISM: Artificial Sequence
<220> FEATURE:
<223> OTHER INFORMATION: SYNTHETIC
<220> FEATURE:
<221> NAME/KEY: MISC_FEATURE
<222> LOCATION: (1)..(1)
<223> OTHER INFORMATION: X = Imidazoylpropionyl

<400> SEQUENCE: 21

Xaa Gly Glu Gly Thr Phe Thr Ser Asp Leu Ser Lys Gln Met Glu
1               5                   10                  15

Glu Ala Val Lys Leu Phe Ile Glu Trp Leu Lys Gln Gly Gly Pro Ser
                20                  25                  30

Ser Gly Ala Pro Pro Pro Ser
            35

<210> SEQ ID NO 22
<211> LENGTH: 39
<212> TYPE: PRT
<213> ORGANISM: Artificial Sequence
<220> FEATURE:
<223> OTHER INFORMATION: SYNTHETIC
<220> FEATURE:
<221> NAME/KEY: MISC_FEATURE
<222> LOCATION: (2)..(2)
<223> OTHER INFORMATION: X = Aib

<400> SEQUENCE: 22

His Xaa Glu Gly Thr Phe Thr Ser Asp Leu Ser Lys Gln Met Glu
1               5                   10                  15

Glu Ala Val Lys Leu Phe Ile Glu Trp Leu Lys Gln Gly Gly Pro Ser
                20                  25                  30

Ser Gly Ala Pro Pro Pro Ser
            35

<210> SEQ ID NO 23
<211> LENGTH: 39
<212> TYPE: PRT
<213> ORGANISM: Artificial Sequence
<220> FEATURE:
<223> OTHER INFORMATION: SYNTHETIC

<400> SEQUENCE: 23

His Gly Glu Gly Thr Phe Thr Ser Asp Leu Ser Gln Gln Leu Glu
1               5                   10                  15

Glu Ala Val Lys Leu Phe Ile Glu Trp Leu Lys Gln Gly Gly Pro Ser
                20                  25                  30
```

```
Ser Gly Ala Pro Pro Pro Ser
        35

<210> SEQ ID NO 24
<211> LENGTH: 39
<212> TYPE: PRT
<213> ORGANISM: Artificial Sequence
<220> FEATURE:
<223> OTHER INFORMATION: SYNTHETIC

<400> SEQUENCE: 24

His Gly Glu Gly Thr Phe Thr Ser Asp Leu Ser Lys Gln Leu Glu Glu
1               5                   10                  15

Glu Ala Val Lys Leu Phe Ile Glu Trp Leu Gln Gln Gly Gly Pro Ser
            20                  25                  30

Ser Gly Ala Pro Pro Pro Ser
        35

<210> SEQ ID NO 25
<211> LENGTH: 39
<212> TYPE: PRT
<213> ORGANISM: Artificial Sequence
<220> FEATURE:
<223> OTHER INFORMATION: SYNTHETIC

<400> SEQUENCE: 25

His Gly Glu Gly Thr Phe Thr Ser Asp Leu Ser Gln Gln Leu Glu Glu
1               5                   10                  15

Glu Ala Val Lys Leu Phe Ile Glu Trp Leu Gln Gln Gly Gly Pro Ser
            20                  25                  30

Ser Gly Ala Pro Pro Pro Ser
        35

<210> SEQ ID NO 26
<211> LENGTH: 39
<212> TYPE: PRT
<213> ORGANISM: Artificial Sequence
<220> FEATURE:
<223> OTHER INFORMATION: SYNTHETIC

<400> SEQUENCE: 26

His Gly Glu Gly Thr Phe Thr Ser Asp Leu Ser Gln Gln Leu Glu Glu
1               5                   10                  15

Glu Ala Val Arg Leu Phe Ile Glu Trp Leu Lys Leu Gly Gly Pro Ser
            20                  25                  30

Ser Gly Ala Pro Pro Pro Ser
        35
```